United States Patent [19]

Triscott

[11] Patent Number: 5,985,582
[45] Date of Patent: Nov. 16, 1999

[54] THROMBIN-BASED ASSAY FOR ANTITHROMBIN III

[75] Inventor: Mark X. Triscott, Ballwin, Mo.

[73] Assignee: Sigma-Aldrich Co., Highland, Ill.

[21] Appl. No.: 08/987,038

[22] Filed: Dec. 9, 1997

[51] Int. Cl.$^6$ .................................................. G01N 33/86
[52] U.S. Cl. .............................. 435/7.1; 436/69; 536/118
[58] Field of Search ....................... 435/7.1, 13; 436/69; 536/118

[56] References Cited

U.S. PATENT DOCUMENTS

| | | | |
|---|---|---|---|
| 4,473,639 | 9/1984 | Sommer et al. | 435/13 |
| 4,496,653 | 1/1985 | Lill et al. | |
| 4,736,018 | 4/1988 | Reutelingsperger | 530/381 |
| 4,918,001 | 4/1990 | Kolde | 435/24 |
| 4,948,724 | 8/1990 | Yin | 435/13 |
| 5,093,237 | 3/1992 | Enomoto | 435/13 |
| 5,221,614 | 6/1993 | Enomoto | 435/13 |
| 5,248,596 | 9/1993 | Esmon et al. | 435/7.92 |
| 5,320,945 | 6/1994 | Dessauer et al. | 435/13 |
| 5,378,829 | 1/1995 | Petitou et al. | 536/118 |
| 5,646,007 | 7/1997 | Enomoto et al. | 435/13 |

FOREIGN PATENT DOCUMENTS

| | | | |
|---|---|---|---|
| 0 509 086 B1 | 10/1991 | European Pat. Off. | C12Q 1/56 |
| 0 657 547 A1 | 6/1994 | European Pat. Off. | C12Q 1/56 |
| 95/00663 | 1/1995 | WIPO | |

OTHER PUBLICATIONS

Hayakawa et al., "Heparin Cofactor II—Dependent Antithrombin Activity of Calcuim Spherulan," Blood Coag. Fibrin. 7:554–560, 1996.

Lane et al. (Eds.) Heparin and Related Polysaccharides in Advances in Experimental Medicine and Biology, 313: 37–47, 167–176, 221–230, 1992.

Linhardt et al., "Structure and Activity of a Unique Heparin–Derived Hexasaccharide," J. Biol. Chem., 261(31): 14448–14454, 1986.

Maimone et al., "Structure of a Dermatan Sulfate Hexasaccharide That Binds to Heparin Cofactor II with High Affinity," J. Biol. Chem, 265(30):18263–71, 1990.

McGuire et al., "Activation of Heparin Cofactor II by Fibroblasts and Vascular Smooth Muscle Cells," J. Biol. Chem., 262(1): 169–175, 1987.

Ofosu et al., (Eds) Heparin and Related Polysaccharides Structure and Activities in Annals of the New York Academy of Sciences, 556:1–17, 104–122, 135–145, 489–491, 1989.

Oosta et al., "Multiple Functional Domains of the Heparin molecule," Proc. Nat'l Acad. Sci. USA, 78(2):829–833, 1981.

Sigma Chemical Catalog pp. 288–289 and 568–569, 1998.

Borg et al. "Improvement in the Identification of Antithrombin Deficient Patients" Abstract No. PS–1768, International Society for Thrombosis and Haemostasis (Jun. 1997).

Church et al. "Antithrombin Activity of Fucoidan" The Journal of Biological Chemistry, vol. 264, No. 6, (Feb. 25, 1989) pp. 3618–3623.

Conrad et al. "Bovine or Human Thrombin in Amidolytic at III Assays Influence of Heparin Cofactor II" Thrombosis Research vol. 41 (1986) pp. 873–878.

Demers et al. "An Antithrombin III Assay Based on Factor Xa Inhibition Provides a more Reliable Test to Identify Congenital Antithrombin III Deficiency Than An Assay Based on Thrombin Inhibition" Thrombosis and Haemostasis, vol. 69, No. 3 (1993) pp. 231–235.

Enomoto et al. "Antithrombin–III Assay Without Influence of Heparin Cofactor II" Thrombosis Research, vol. 57 (1990) pp. 729–736.

Friberger et al. "Antithromin Assay — The Use of Human or Bovine Thrombin and the Observation of a "Second" Heparin Cofactor" Thrombosis Research, vol. 25, (1982) pp. 433–436.

Hayakawa et al. "Selective Activation of Heparin Cofactor II by a Sulfated Polysaccharide Isolated from the Leaves of Artemisisa Princeps" Blood Coagulation and Fibrinolysis, vol. 6 (1995) pp. 643–649.

Tollefsen et al. "Activation of Heparin Cofactor II by Dermatan Sulfate" The Journal of Biological Chemistry, vol. 258, No. 11 (Jun. 10, 1983) pp. 6713–6716.

Tollefsen et al. "Heparin Cofactor II; Purification and Properties of a Heparin–Dependnet Inhibitor of Thrombin in Human Plasma" The Journal of Biological Chemistry, vol. 257, No. 5 (Mar. 10, 1982) pp. 2162–2169.

Triscott et al. "Improved Differentiation Between Normal and Abnormal Antithrombin III Levels Using a Thrombin Based Chromogenic Assay" Blood, vol. 90, No. 10, Suppl. 1, Pt. 2 (Nov. 15, 1997) Abstract No. 3171.

Ukita "ATIII, Heparin" Rinsyo Byori, Special vol. 70 (1987) pp. 173–180.

Derwent WPI Acc. No. 89–254696/198935 Abstract, 1989.

Derwent WPI Acc. No. 77–37344Y/197721 Abstract, 1977.

Rosenberg et al. "The Heparine–Antithrombin System: A Natural Anticoagulant Mechanism" Hemostasis and Thrombosis: Basic Principles and Clinical Practice, Third Edition (1994) pp. 837–860.

*Primary Examiner*—Christopher L. Chin
*Assistant Examiner*—Bao-Thuy L. Nguyen
*Attorney, Agent, or Firm*—Senniger, Powers, Leavitt & Roedel

[57] ABSTRACT

Thrombin-based assays are disclosed for determining antithrombin III (ATIII) present in a plasma sample. The assays involve a heparin derivative which, like heparin, effectively enhances the antithrombin activity of ATIII, but which, unlike heparin, does not substantially enhance the antithrombin activity of Heparin cofactor II (HCII). In the present assay, HCII contributes about 15% or less to the determined antithrombin activity. A lyophilized reagent composition, useful in the ATIII assay and comprising thrombin and a heparin derivative, or alternatively comprising thrombin and heparin, is also disclosed. A high-calibrator plasma reference useful in the ATIII assays and in assays for other plasma constituents is also disclosed. Kits employing the several aspects of the invention are disclosed as well.

32 Claims, 7 Drawing Sheets

THROMBIN-BASED ASSAY FOR ANTITHROMBIN III

BACKGROUND OF THE INVENTION

The present invention generally relates to protocols for evaluating the hemostasis of a patient at risk of developing thrombosis, and specifically, to diagnostic assays for determining the level of antithrombin III present in a plasma sample withdrawn from a patient. The invention particularly relates, in a preferred embodiment, to a chromogenic thrombin-based (ie, type IIa) assay for determining antithrombin III. The invention also relates to a heparin derivative, to a reagent composition and to a high-calibrator plasma reference useful in such assays and to kits employing the same.

The advantageous formation of blood clots during wound healing and the undesirable development of thrombi in connection with thrombosis both involve the proteolytic action of the serine protease thrombin on fibrinogen. The level of thrombin present in vivo is primarily regulated by the heparin-catalyzed thrombin inhibitor, antithrombin III (ATIII). Hence, the level of ATIII present in vivo is of significant clinical importance for diagnosing and monitoring patients at risk for excessive bleeding, due to abnormally high levels of ATIII, or at risk for developing thrombi, due to abnormally low levels of ATIII.

One type of assay for antithrombin III is based on the capability of ATIII present in a plasma sample to inhibit the proteolytic activity of exogenously added thrombin in the presence of heparin. The residual, uninhibited thrombin is then determined by methods typically involving, for example, thrombin-specific chromogenic substrates and spectrophotometric analyses, or alternatively, fibrinogen and clot-forming analyses.

However, such thrombin-based ATIII assays—also referred to as factor IIa ATIII assays—are inaccurate due to the activity of a second heparin-catalyzed thrombin-inhibitor, heparin cofactor II (HCII). See Tollefson et al., *Heparin Cofactor II*, Jrnl. Biol. Chem. 257:5, pp. 2162–2169 (1982). That is, thrombin-based assays known in the art measure the levels of exogenous thrombin remaining after the thrombin has reacted with both ATIII and HCII—not just with ATIII. The inaccuracy of such assays are of particular clinical concern for ATIII-deficient patients. In cases where HCII is in the high normal range and ATIII is determined using thrombin-based assays known in the art, an ATIII deficiency can be masked by the HCII antithrombin activity.

Several approaches have been developed for avoiding the masking effect of HCII. One proposed approach for a factor IIa assay involved the use of bovine thrombin in the presence of relatively low concentrations of heparin. See Friberger et al., *Antithrombin Assay—The Use of Human or Bovine Thrombin and the Observation of a "Second" Heparin Cofactor*, Thrombosis Research 25, pp. 433–436 (1982). This approach, however, did not provide a commercially recognized solution to the problem.

Another approach is described in U.S. Pat. No. 5,646,007 to Enomoto et al., wherein a chromogenic thrombin-based ATIII assay is conducted in the presence of salt at a concentration ranging from about 0.2 M to about 0.9 M, and preferably at a concentration greater than about 0.3. While this approach offers some benefits with respect to limiting the effect of HCII activity against thrombin, the sensitivity of chromogenic assays for thrombin decreases as the concentration of salt increases, due to an allosteric effect on thrombin in the presence of such higher salt concentrations. Reduced sensitivity is of particular commercial significance for ATIII assays performed using automated analyzers.

According to yet another approach, the ATIII assay is performed using exogenously added factor Xa as an indicator instead of thrombin. See Demers et al., *An Antithrombin III Assay Based on Factor Xa Inhibition Provides A More Reliable Test to Identify Congenital Antithrombin III Deficiency Than an Assay Based on Thrombin Inhibition*, Thrombosis and Hemostasis 69:3 pp. 231–235 (1993). Unlike thrombin, factor Xa is not inhibited by HCII. However, factor Xa-type ATIII assays are more expensive than factor IIa-type assays. Moreover, factor Xa can be less stable than thrombin under certain conditions, and the factor Xa-based assays can require a greater degree of dilution. As such, factor Xa ATIII assays are less suitable for use with automated analyzers.

Assays for determining ATIII, and in fact, assays for determining other plasma constituents, have other common problems when the assay protocol involves correlation of a determined amount using a standard curve developed from reference plasma samples of known constituent concentration. Because reference plasmas known in the art typically have high-end constituent concentrations of less than about 105% of normal, it is not possible to directly determine a plasma constituent which is substantially above the normal concentration range of that constituent (e.g. about 110% or more). Instead of making such determination directly, it is presently necessary to dilute the patient plasma sample (e.g. 1:1 in saline), reperform the determination, and then multiply the determined amount by the dilution factor (e.g. 2 for a 1:1 dilution).

SUMMARY OF THE INVENTION

It is therefore an object of the present invention to provide an improved thrombin-based ATIII assay which provides for detection of ATIII in human plasma samples, and, particularly, in plasma samples of ATIII deficient patients. It is also an object of the invention to provide thrombin-based ATIII assays which are not influenced by the antithrombin activity of HCII, which can be suitably performed with automated analyzers, and which are simpler to perform, yet suitably sensitive, accurate, reproducible and relatively inexpensive.

It is a further object of the invention to provide simpler protocols for determining ATIII and other plasma constituents present at higher-than-normal concentrations.

Briefly, therefore, the present invention is directed to a method for determining antithrombin III in a plasma sample. According to one approach for the method, the plasma sample is combined with thrombin and with a heparin derivative to form an assay mixture. A complex is formed between antithrombin III and thrombin in the assay mixture. The uncomplexed thrombin in the assay mixture is then determined and the determined uncomplexed thrombin is correlated to the antithrombin III in the plasma sample.

In an alternative approach, ATIII in a plasma sample is determined by preparing an assay mixture comprising the plasma sample, exogenous thrombin, and a heparin derivative. The heparin derivative is effective for enhancing the formation of a thrombin-antithrombin III complex, but is substantially less effective than unmodified heparin for enhancing heparin cofactor II activity against thrombin. The assay mixture is then incubated, and the uncomplexed thrombin in the incubated assay mixture is determined. The determined uncomplexed thrombin is correlated to the antithrombin III in the plasma sample.

In a further approach for determining antithrombin III in a plasma sample, an assay mixture comprising the plasma sample, exogenous thrombin, and a heparin derivative is prepared. The assay mixture is incubated, and then the uncomplexed thrombin in the incubated assay mixture is determined. The determined uncomplexed thrombin is correlated to the antithrombin III in the plasma sample. Heparin cofactor II contributes about 15% or less to the determined antithrombin activity of antithrombin III.

According to yet another approach for determining antithrombin III in a plasma sample, a modified heparin composition prepared by enzymatically digesting heparin is obtained, an assay mixture comprising the plasma sample, exogenous thrombin, and the modified heparin composition is prepared. The assay mixture is then incubated, and the uncomplexed thrombin in the incubated assay mixture is determined. The determined uncomplexed thrombin is correlated to the antithrombin III in the plasma sample.

The invention is also directed to a modified heparin compound. The modified compound comprises a heparin derivative which is effective for enhancing the antithrombin III activity against thrombin, but which is less effective than unmodified heparin for enhancing the heparin cofactor II activity against thrombin.

The heparin derivative can be one prepared by reacting heparin with an enzyme to form the heparin derivative and one or more disaccharides.

The heparin derivative can also be one prepared by reacting heparin with a chondroitinase.

The invention is further directed to a modified heparin composition prepared by enzymatically digesting heparin.

Another aspect of the invention is directed to a method for preparing a heparin derivative. The method comprises forming a solution comprising heparin, adding an enzyme to the heparin solution, and allowing the enzyme to react with heparin to form a heparin derivative and an unsaturated disaccharide.

According to another approach, the method for preparing a heparin derivative comprises reacting heparin with a chondroitinase.

The invention is directed as well to a reagent useful in a thrombin-based antithrombin III assay. The reagent is a lyophilized composition comprising (1) thrombin and (2) heparin or a heparin derivative.

A further aspect of the invention is directed to a kit for a thrombin-based antithrombin III assay useful to determine antithrombin III in a plasma sample. The kit includes (1) a diluent composition comprising a chondroitinase ACI-treated heparin and an alkali metal-halide salt, (2) a reagent composition comprising an chondroitinase ACI-treated heparin, an alkali metal-halide salt and thrombin, and (3) a chromogenic thrombin substrate.

The invention is directed, in a different aspect, to a method for preparing a high-calibrator reference plasma suitable for use as a standard for determination of a plasma constituent. A normal reference plasma is obtained and a volume, $V_1$, of the normal reference plasma is lyophilized. The lyophilized normal reference plasma is reconstituted to form a reconstituted plasma of a volume, $V_2$, where the ratio of $V_2:V_1$ ranges from about 7:8 to about 1:8.

In another method for preparing a high-calibrator reference plasma suitable for use as a standard for determination of a plasma constituent, a normal reference plasma comprising a plasma constituent at a concentration ranging from about 90% of normal to about 110% of normal is obtained. A volume, $V_1$, of the normal reference plasma is lyophilized, and the lyophilized normal reference plasma is then reconstituted to form a reconstituted plasma of a volume, $V_2$. $V_2$ is less than $V_1$ and the reconstituted plasma comprises the plasma constituent at a concentration of about 120% of normal or greater. The plasma constituent is preferably ATIII.

The invention is directed, moreover, to a kit that includes (1) a lyophilized reference plasma comprising a plasma constituent at a concentration ranging from about 90% of normal to about 110% of normal, and (2) instructions to reconstitute the lyophilized reference plasma with a volume sufficient to form a reconstituted plasma which includes the plasma constituent at a concentration of about 120% of normal or greater.

The present invention, as described and claimed herein, is advantageous over prior art methods for determining ATIII, and solves the several problems associated with such known methods. In particular, the present invention provides compounds, reagents and methods by which the HCII activity against thrombin is essentially removed. Moreover, this is accomplished without sacrificing sensitivity of the ATIII assay and without using expensive and potentially unstable reagents. The reagents of the present invention can be used to determine ATIII according to simplified protocols. The high-calibrator plasma samples of the invention can be used to simplify the protocols for determining ATIII and/or other plasma constituents for patient plasma samples having constituent values greater than about 110% of normal. Other features and objects of the present invention will be in part apparent to those skilled in the art and in part pointed out hereinafter.

(triangles), and as "HCII-normal/untreated/0.310M (open squares). Values are reported in percent normals.

Figure 3:
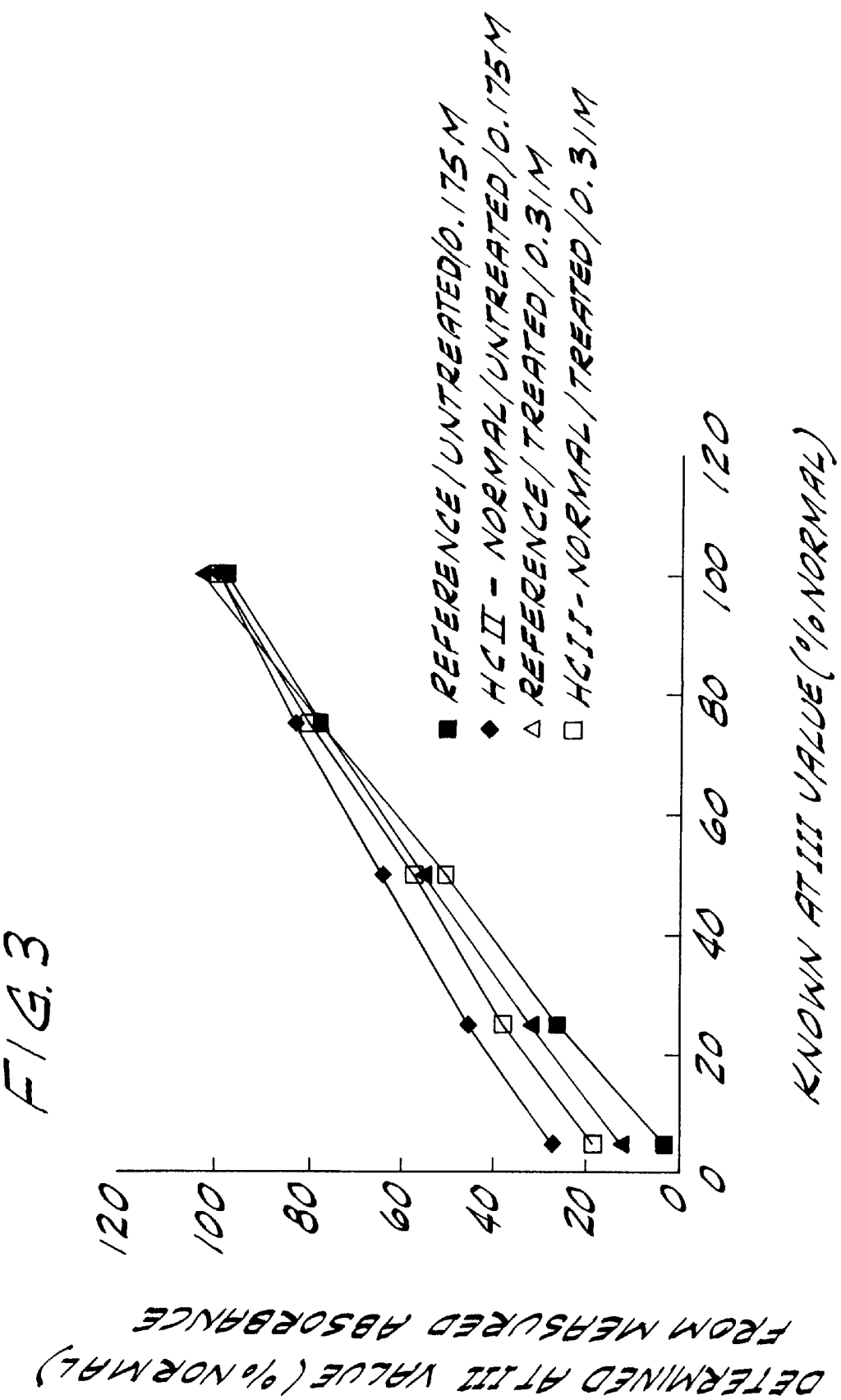

FIG. 3 shows determined ATIII values for plasma samples having various known ATIII concentrations. Reference samples were prepared by dilution of a normal reference plasma with saline, and HCII-normal samples were prepared by dilution of a normal reference plasma with ATIII-deficient plasma (Affinity Biologicals) having less than 1% normal ATIII level, but containing normal levels of heparin cofactor II (HCII) as well as other plasma constituents. The reference samples and the HCII-normal samples were assayed using an assay mixture including chondroitinase AC-treated heparin and 310 mM sodium chloride, and, independently, using an assay mixture including unmodified heparin and 175 mM sodium chloride. The standard curves developed are designated as "reference/untreated/0.175M" (closed square), as "HCII-normal/untreated/0.175M" (diamonds), as "reference/treated/0.310M" (triangles), and as "HCII-normal/treated/0.310M" (open squares).

Figure 4:
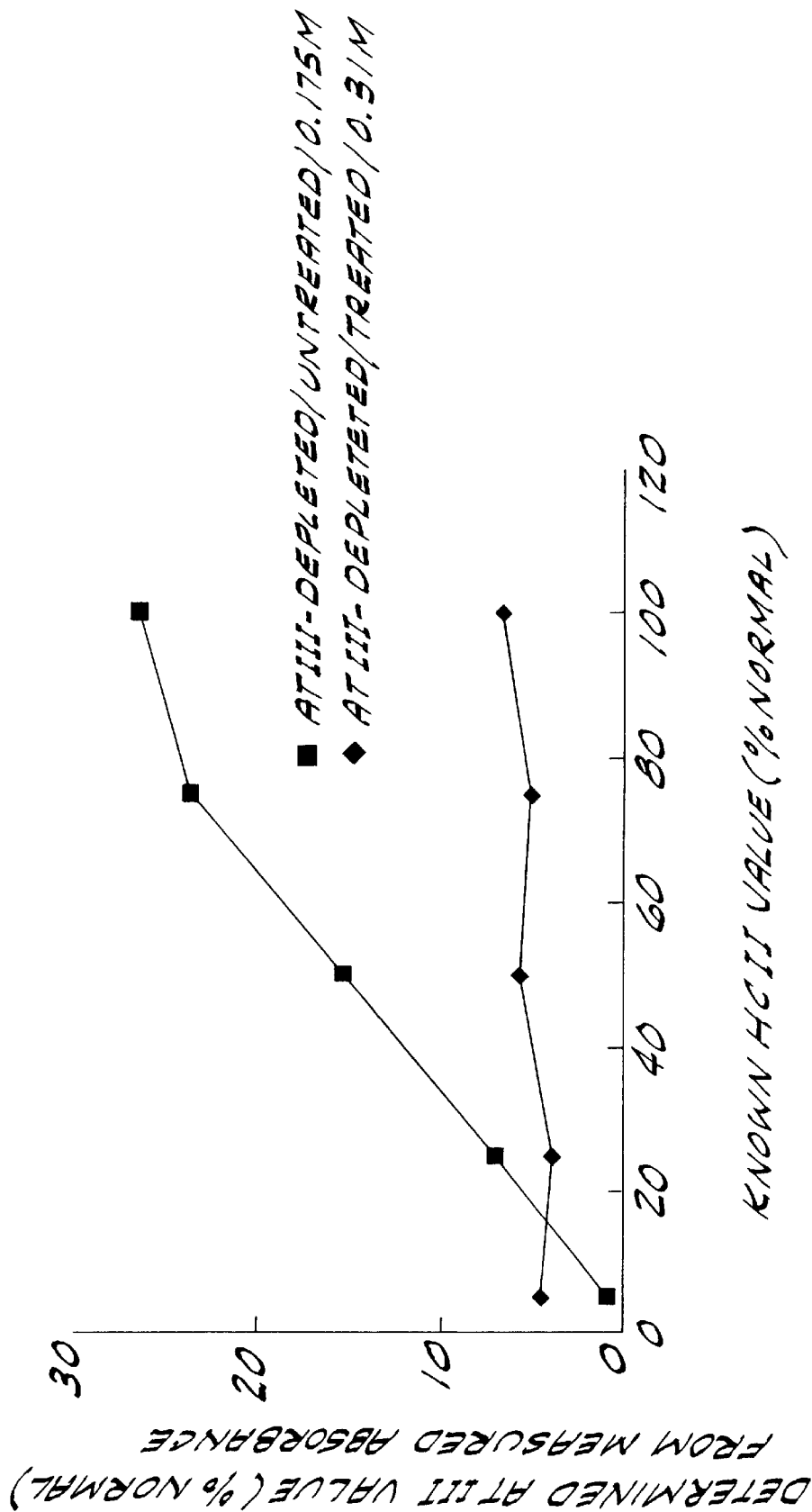

FIG. 4 shows determined ATIII values for ATIII-depleted plasma samples having various known concentrations of HCII. ATIII-depleted samples were prepared by diluting ATIII-immunodepleted plasma (Affinity Biologicals) having less than 1% normal ATIII level, but containing normal levels of heparin cofactor II (HCII) as well as other plasma constituents. The ATIII-depleted samples were assayed using an assay mixture including chondroitinase AC-treated heparin and 310 mM sodium chloride, and, as an independent control, using an assay mixture including unmodified heparin and 175 mM sodium chloride. The standard curves are referred to as "ATIII-depleted/untreated/0.175M" (closed square), and as "ATIII-depleted/treated/0.310M" (diamonds).

Figure 5:
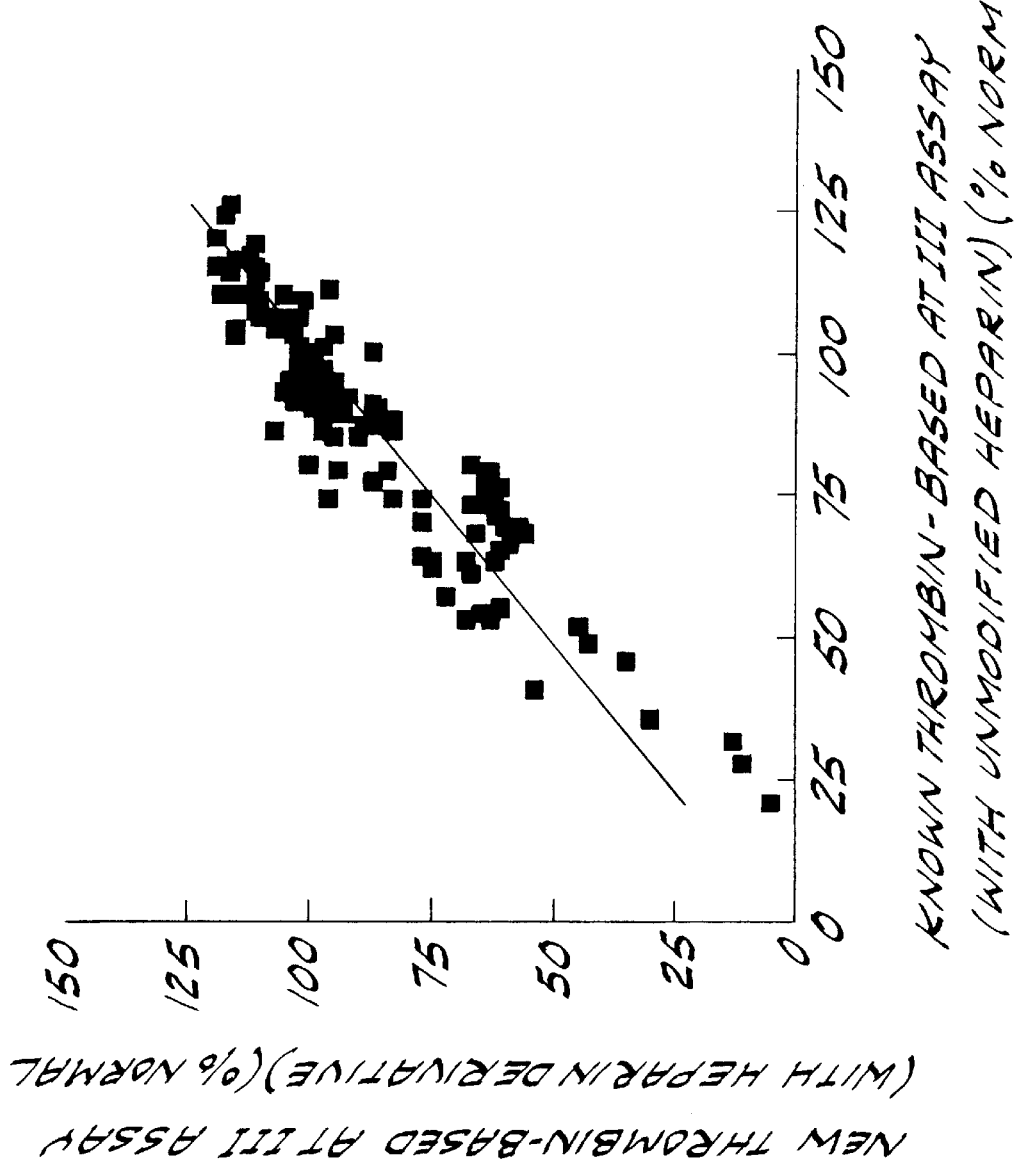

FIG. 5 shows the results of a correlation study comparing the ATIII assay of the present invention (using chondroitinase-AC treated heparin with a NaCl concentration of 220 mM) to a known thrombin-based assay (using unmodified heparin with a NaCl concentration of 175 mM). Regression analysis of the data indicates a correlation coefficient, r, between the ATIII assay of the present and the known thrombin-based assay of r=0.93.

Figure 6:
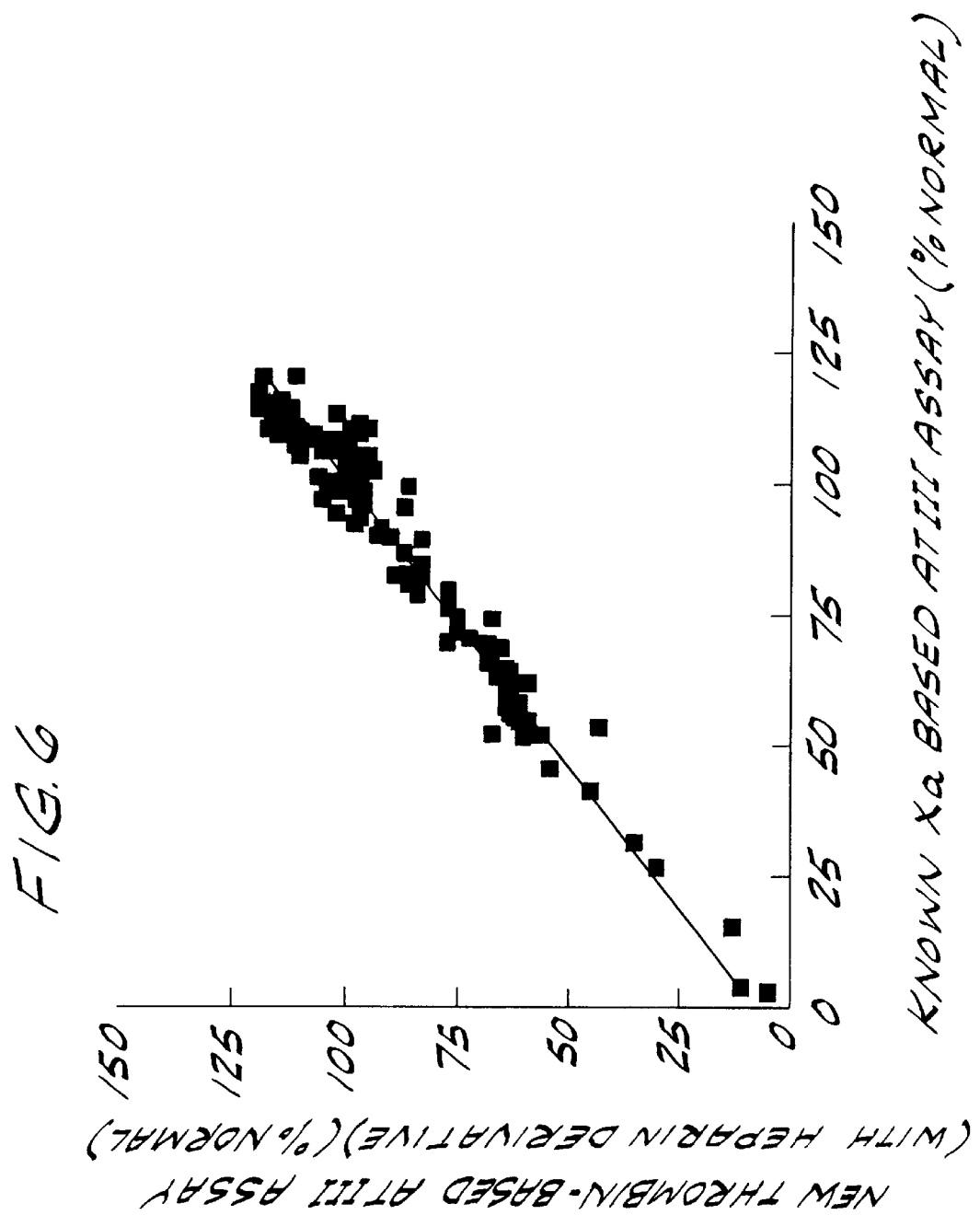

FIG. 6 shows the results of a correlation study comparing the ATIII assay of the present invention (using chondroitinase AC-treated heparin with a NaCl concentration of 220 mM) to a known Factor Xa-based assay. Regression analysis of the data indicates a correlation coefficient, r, between the ATIII assay of the present and the known Factor Xa-based assay of r=0.98.

Figure 7:
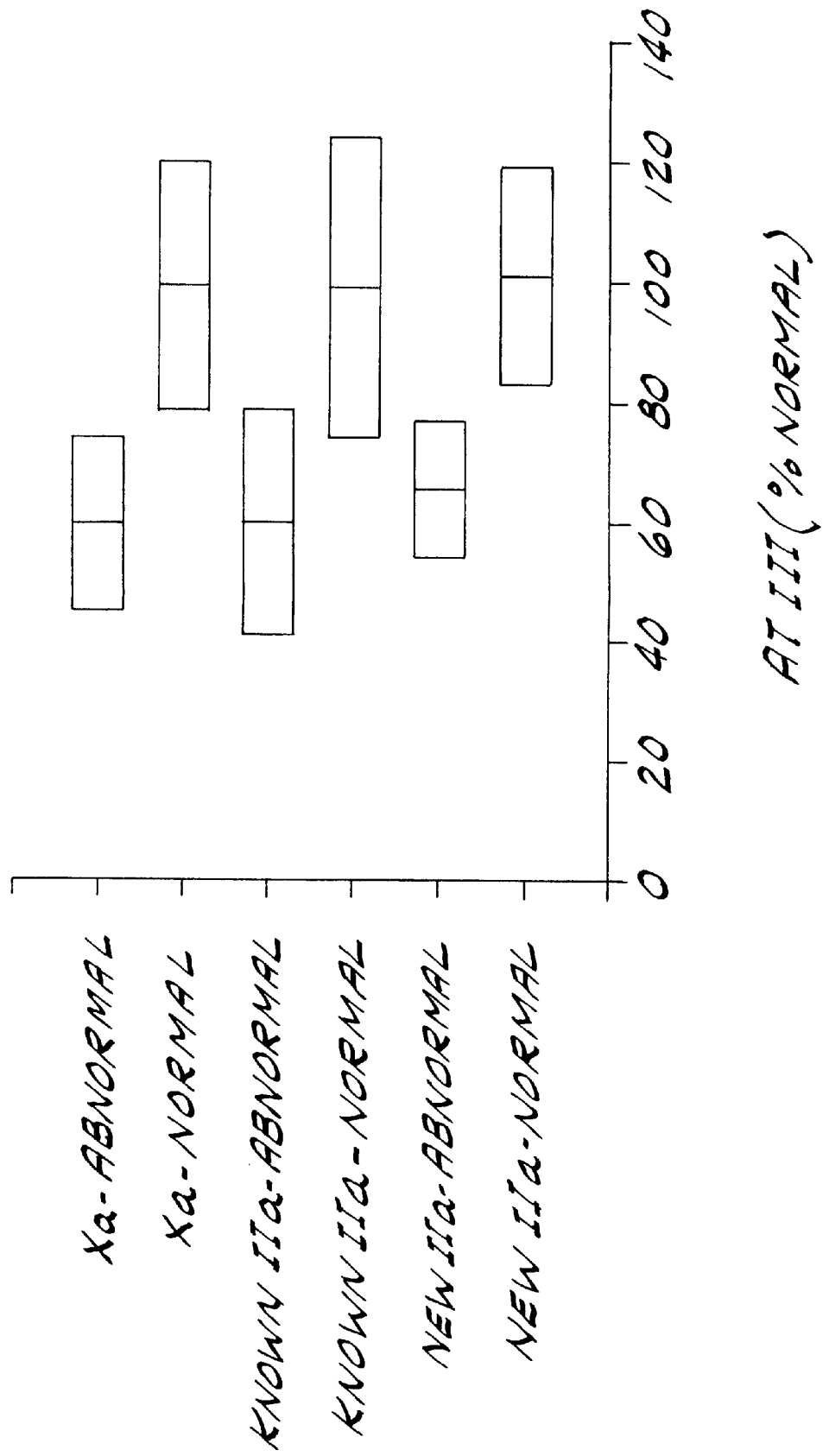

FIG. 7 compares normal and abnormal determined ATIII ranges for a population of healthy volunteers assayed using a Factor Xa-based assay, a known thrombin-based assay (using unmodified heparin), and the thrombin-based assay of the present invention (using a heparin derivative prepared with chondroitinase AC). Abnormal samples were selected as <75% normal based on the Factor Xa assay.

DETAILED DESCRIPTION OF THE INVENTION

The present invention involves a modified heparin compound which, like heparin, effectively enhances the antithrombin activity of ATIII, but which, unlike heparin, does not substantially enhance the antithrombin activity of HCII. More specifically, the modified heparin compound of the present invention is a heparin derivative which enhances HCII activity against thrombin substantially less than unmodified heparin enhances the HCII activity against thrombin. The heparin derivative preferably enhances the HCII antithrombin activity at least about 2 times less than unmodified heparin, more preferably at least about 4 times less than unmodified heparin, and most preferably at least about 5 times less than unmodified heparin.

The modified heparin compound of the present invention is prepared, according to a preferred embodiment, by enzymatically digesting heparin to form a heparin derivative and one or more unsaturated disaccharides. (See Example 1). The type of heparin used as a starting material for preparing the heparin derivative is not narrowly critical. The heparin can be heterogeneous heparin or low molecular weight heparin. The heparin can, moreover, be from any animal source, including for example, human, bovine and/or porcine heparin. The heparin is preferably heterogeneous heparin and is preferably obtained from either bovine or porcine. Heterogeneous porcine heparin is most preferred, and is available commercially from Sigma Chemical, St. Louis, Mo. (Catalog No. H3393).

A buffered solution comprising unmodified heparin is preferably formed by combining heparin with a buffer and adjusting the pH to range from about 4 to about 10, and most preferably to be about 7.2. While any suitable buffer may be employed, a sodium phosphate buffer is preferred. The concentration of heparin in the solution preferably ranges from about 0.01 U/ml to about 100,000 U/ml, more preferably from about 1 U/ml to about 20,000 U/ml, and is most preferably about 10,000 U/ml. One unit of heparin activity, U, is defined as per the United States Pharmacopeia (USP).

An enzyme having an activity which cleaves one or more disaccharides from heparin to form a heparin derivative is added to the heparin-containing buffered solution to form a reaction solution. The enzyme is preferably a chondroitinase enzyme, and is, more preferably, a chondroitinase enzyme derived from *Flavobacterium heparinium*. Chondroitinase ACI is a most preferred enzyme and is available commercially from Sigma Chemical, St. Louis, Mo., as chondroitinase AC. (Catalog No. C2780). Other enzymes, including chondroitinase ABC, chondroitinase B, chondroitinase C and chondroitinase ACII, may also be suitable for practicing the invention.

When the preferred chondroitinase ACI is employed, the concentration of enzyme in the reaction solution preferably ranges from about 0.01 unit/ml to about 100 unit/ml, more preferably from about 0.1 unit/ml to about 10 unit/ml, and is most preferably about 1 unit/ml. One unit of chondroitinase ACI activity is defined herein as an amount which causes a delta OD232 of 1.0/min acting on chondroitin sulfate A at pH 7.3 at 37° C. The concentrations and/or volumes can be adjusted to form a reaction solution in which the ratio of the chondroitinase ACI to the heparin preferably ranges from about 1:10 to about 1:100,000, more preferably from about 1:1000 to about 1:20,000, and is most preferably about 1:10,000 units.

The enzymatic digestion is preferably effected by mixing the reaction solution and then incubating the reaction solution at a temperature preferably ranging from about 12° C. to about 56° C., more preferably from about 30° C. to about 45° C., and preferably at a temperature of about 37° C. for a period of time ranging from about 12 hours to about 60 hours, preferably from about 24 hours through about 48 hours, and most preferably for about 40 hours. Following digestion for the above-specified periods, the enzyme is preferably inactivated by suitable methods known in the art. A preferred inactivation step includes heating the reaction solution to an elevated temperature for a period sufficient to inactivate the enzyme. Chondroitinase ACI can be inactivated, for example, by submersing the container or vial that holds the reaction solution in a boiling water bath for about 5 minutes.

The resulting modified heparin composition, which comprises a heparin derivative and one or more disaccharides, can be characterized based on its spectrophotometric absorbance at OD232. The modified heparin composition preferably has an increased absorbance at OD232 relative to the reaction solution prior to enzymatic digestion. The OD232 absorbance of the modified heparin composition (ie, measured after digestion) preferably increases by an amount ranging from about 0.05% to about 50% of its original value, more preferably from about 0.1% to about 25% of its original value, and is most preferably about 10% of its original value. If desired, the heparin derivative can be isolated from the modified heparin composition using separation protocols known in the art. For example, the heparin derivative can be separated by size using chromatographic protocols and/or by sulfate content. Preferably, however, the modified heparin composition containing the heparin derivative is used directly in an assay mixture, as described below.

When the heparin derivative is prepared by enzymatic digestion of heparin, the unmodified heparin to which the heparin derivative is compared for HCII-enhancing activity is preferably unmodified heparin which is analogous to the heparin from which the heparin derivative is prepared. That is, the unmodified heparin to which the heparin derivative is compared is preferably of the same molecular-weight heterogenicity as (e.g. heterogeneous heparin versus low-molecular weight heparin), and is preferably species-homogolous or species-autogolous to the heparin used as a starting material for preparing the heparin derivative. For example, when the heparin derivative is derived from heterogeneous porcine heparin, the HCII-enhancing activity of the heparin derivative is preferably compared to the HCII-enhancing activity of heterogeneous, unmodified porcine heparin.

The heparin derivative of the present invention, while preferably derived as described above from unmodified heparin, can also be prepared by other methods known in the art. For example, the heparin derivative can be isolated, as described above, and then synthetically prepared. The synthetic preparation can involve organic synthesis protocols known in the art and can, if appropriate, also involve recombinant DNA technology, including, but not limited to the use of genetically engineered plasmids or other vectors, and corresponding host cell systems. When the heparin derivative is prepared by methods which do not involve using unmodified heparin as a starting material, the unmodified heparin to which the heparin derivative is compared for HCII-enhancing activity is preferably unmodified heterogeneous bovine heparin or unmodified heterogeneous unmodified porcine heparin, and preferably heterogeneous unmodified porcine heparin.

The heparin derivative can be advantageously employed in an improved thrombin-based ATIII assay. (See Example 2 and Example 3). Generally, the ATIII assay is performed by obtaining a plasma sample, combining the plasma sample with a heparin derivative and with thrombin to form an assay mixture, forming a complex between ATIII and thrombin without forming a diagnostically significant degree of complex between HCII and thrombin, determining the uncomplexed thrombin present in the assay mixture, and correlating the determined uncomplexed thrombin to the antithrombin III present in the plasma sample.

The plasma sample is preferably a human plasma sample, and can be obtained from blood drawn from a patient according to conventional methods known in the art. Preferably, the plasma sample is collected and stored in accordance with NCCLS (National Committee for Clinical Laboratory Standards, Inc., Wayne, Pa.)guidelines H21-A2. According to a preferred method, venous blood is drawn into a plastic or siliconized syringe, avoiding stasis and contamination with tissue fluid. The blood (9 parts by volume) is immediately transferred to a tube containing a 3.2% or 3.8% solution of sodium citrate (1 part by volume). Alternatively, the blood may be drawn into commercial vacuum tubes containing the citrate solution. The citrated blood is mixed and then centrifuged at 2500×g for 15 minutes to obtain a citrated plasma. The plasma is transferred to a test tube for storage at a temperature ranging from about 2° C. to about 8° C. for up to 4 hours after collection, or alternatively, at about −20° C. for up to one month after collection, and then thawed at 37° C. for 30 minutes before use. Because human plasma samples include both ATIII and HCII antithrombin activity, the present method is most advantageously employed with patients known to be or suspected of being at risk of thrombosis, and particularly, with patients known to have or suspected of having an antithrombin deficiency. Known antithrombin III deficiencies include, for example, genetic deficiencies (e.g. Type I and Type II) and acquired deficiencies such as those occurring in consumptive coagulopathies (e.g. DVT, DIC, pulmonary emboli), other disease states (e.g. severe liver disease, nephrotic syndrome), surgery, pregnancy, trauma and certain courses of therapy (e.g. L-asparaginase). ATIII levels may be lower in infants up to six months in age and in women. ATIII levels also decrease with age.

The plasma sample can be used to form the assay mixture directly as an undiluted plasma sample or after diluting, as a diluted plasma sample. While the plasma sample will typically be one which is withdrawn from a patient to be determined for ATIII for diagnostic or monitoring purposes, the plasma sample can also, as discussed in more detail below, be a standard plasma sample having a known concentration of ATIII for development of a correlation standard.

The plasma sample is combined with a heparin derivative and with exogenous thrombin to form an assay mixture. The heparin derivative, described above, is preferably present in the assay mixture in an excess, non-limiting amount, relative to the amount of ATIII present in the plasma sample. The heparin derivative is, more specifically, preferably present in the assay mixture at a concentration preferably ranging from about 0.1 U to about 10 U, more preferably from about 0.2 U to about 1.2 U, and most preferably from about 0.3 U to about 0.7 U, where the unit, U, is defined in the same manner as for heparin. When the preferred heparin derivative, chondroitinase ACI-treated heparin, is employed, the concentration of the chondroitinase ACI-treated heparin is most preferably about 0.5 U. The thrombin can be any suitable thrombin, including human, bovine, porcine, horse or goat thrombin. Bovine thrombin is preferred, and is commercially available from Sigma Chemical, St. Louis, Mo. (Cat. No. T 4648, and others). The thrombin is present in the assay mixture in stoichiometric molar excess relative to that required to complex with ATIII, whereby residual, uncomplexed thrombin will be present in the assay mixture after the ATIII-thrombin reaction is complete. In a preferred embodiment, the concentration of thrombin present in the assay mixture preferably ranges from about 1 IU/ml to about 25 IU/ml, and more preferably from about 5 IU/ml to about 15 IU/ml. The thrombin is most preferably present in the reaction mixture at a concentration of about 8 IU/ml.

The particular order in which the plasma sample, heparin derivative and thrombin are combined is not narrowly critical. For example, the plasma sample can be combined with a heparin derivative and with thrombin by adding the heparin derivative to the plasma sample first, incubating to form a heparinized plasma sample, and then adding thrombin to the heparinized plasma sample. Alternatively, the heparin derivative and thrombin can be added to the plasma sample at about the same time. In another, preferred, approach, the assay mixture is formed by adding a heparin derivative to the plasma sample, with or without incubating, to form a heparinized plasma sample and then adding both thrombin and additional heparin derivative to the heparinized plasma sample.

The assay mixture preferably also includes a salt. The salt can be an organic salt such as citrate. The salt can also be, additionally or alternatively, an inorganic salt. Preferred inorganic salts include alkali metal halides such as sodium halides or potassium halides, with sodium chloride, NaCl, or potassium chloride, KCl, being more preferred. Sodium chloride is a most preferred salt. The concentration of salt present in the assay mixture during formation of the ATIII-thrombin complex is preferably sufficient for the heparin derivative to enhance the ATIII activity for thrombin without substantially enhancing the HCII activity for thrombin. An optimized concentration of salt is one in which (1) the heparin derivative complexes with ATIII, but (2) does not complex to a diagnostically significant degree with HCII, yet (3) is not so high as to effect adverse allosteric changes to thrombin. A diagnostically significant degree of complexing is, as explained in more detail below, generally one in which HCII contributes 15% or less of the determined ATIII/HCII antithrombin activity, more preferably 10% or less of the determined antithrombin activity, even more preferably 5% or less of the determined antithrombin activity, and most preferably 2% or less of the combined antithrombin activity. (See Example 4 and Example 5, showing the effect of salt concentration on an ATIII assay using, respectfully, unmodified heparin and a heparin derivative). In a preferred embodiment, where the heparin derivative is a chondroitinase-treated heparin (e.g. chondroitinase ACI-treated heparin) and the salt is an alkali metal halide (e.g. NaCl), the concentration of salt preferably ranges from about 0.175 M to about 0.3 M, more preferably from about 0.2 M to about 0.25 M, and most preferably about 0.22 M. While the recited ranges are presently preferred for the preferred embodiment, the concentration of salt in the reaction mixture can, in general, be optimized by a person of skill in the art, according to the guidelines presented herein.

The assay mixture can also include other compounds and/or reagents known in the art. For example, the assay mixture preferably includes a buffer with the pH of the assay mixture being adjusted to range from about 6 to about 10, and most preferably to be about 8.2. Suitable buffers include, for example, tris, phosphate, barbital, glycylglycine, BES, MOPS, TES, HEPES, TAPSO and TAPS. TAPS is a preferred buffer. The assay mixture can also include surfactants (e.g. Tween 80 or Triton X-100 (polyoxyethylene(10) isooctylphenyl ether)), cheating agents (e.g. EDTA), preservatives (e.g. sodium azide), and other agents commonly employed in plasma assays as diluents and for other reasons known in the art, such as bovine serum albumin, gelatin, dextran and/or polyethyleneglycol. The concentrations of these additional compounds and/or reagents can be determined by a person of skill in the art.

A preferred assay mixture comprises the plasma sample, an chondroitinase ACI-treated heparin, thrombin and NaCl as described above, as well as suitable amounts of TAPS, EDTA, Tween 80, gelatin, sodium azide, dextran and bovine serum albumin. (See Example 3).

For convenience, the assay mixture is preferably formed from prepared compositions that include a heparin derivative and, optionally, thrombin, in combination with each of the other compounds to be added to the plasma sample. For example, a heparin-derivative diluent composition can be prepared that includes a heparin derivative and salt in an appropriate buffer, and additionally, surfactants, chelating agents, preservatives and other compounds commonly employed. The concentration of heparin derivative in the diluent composition preferably ranges from about 0.05 U/ml to about 10 U/ml, more preferably from about 0.2 U/ml to about 1.2 U/ml, and is most preferably about 0.5 U/ml. A preferred heparin-derivative diluent composition includes chondroitinase ACI-treated heparin, NaCl, TAPS, EDTA, Tween 80, gelatin, sodium azide, dextran and bovine serum albumin. (See Example 2).

A heparin-derivative-thrombin reagent composition can include thrombin in addition to each of the components of the diluent composition. The concentration of thrombin in the reagent composition preferably ranges from about 1 IU/ml to about 100 IU/ml, more preferably from about 4 IU/ml to about 25 IU/ml, and is most preferably about 8 IU/ml. Accordingly, a preferred heparin-derivative-thrombin reagent composition includes thrombin, chondroitinase ACI-treated heparin, NaCl, TAPS, EDTA, Tween 80, gelatin, sodium azide, dextran and bovine serum albumin. (See Example 2). The heparin derivative in the diluent composition or in the reagent composition is preferably provided to these compositions as a modified heparin composition resulting from the preparation of the heparin derivative, without isolation of the heparin derivative, as described above. If desired, the plasma sample can be diluted with the diluent composition before forming the assay mixture. The assay mixture can be formed by combining a plasma sample, whether diluted or not, with the reagent composition.

Regardless of the exact nature in which the assay mixture is prepared, a complex is formed between antithrombin present in the plasma sample (now part of the assay mixture) and thrombin added to the plasma sample. The nature of the complex formed is not critically significant. Without being bound by theory, the complex is believed to be based on ionic and/or covalent interactions between ATIII and thrombin. The heparin derivative is thought to induce a conformational change in ATIII, and/or to act as a polysaccharide bridge between thrombin and ATIII. The complex is preferably formed by incubating the assay mixture at a temperature and time sufficient, in combination to allow complex formation. Typically, and preferably, the complex is formed by incubating the assay mixture for periods ranging from about 15 seconds to about 30 minutes, more preferably from about 1 minute to about 3 minutes, and most preferably for about 2 minutes at temperatures ranging from about 18° C. to about 45° C., and more preferably at temperatures ranging from about 34° C. to about 40° C. and most preferably at a temperature of about 37° C.

Significantly, the heparin derivative effectively enhances the ATIII activity against thrombin but does not substantially enhance the HCII activity against thrombin. As such, no detectable complex, or at most, minimally detectable complex is formed between HCII and thrombin. (See FIG. 1, Example 2). The degree of HCII-thrombin complexing is preferably less than would be diagnostically significant. For plasma samples of patients known or suspected of being ATIII-deficient, a diagnostically significant degree of HCII-thrombin complex formation is one in which HCII accounts for more than about 15% of the determined ATIII/HCII antithrombin activity, as measured using a thrombin-based ATIII assay, such as shown in Example 2. Reducing the contribution of HCII to about 15% or less offers advantages over presently known thrombin-based ATIII assays, in which HCII accounts for about 25% to 30% of the determined ATIII activity. HCII preferably accounts for about 10% or less of the determined antithrombin activity, more preferably about 5% or less of the determined antithrombin activity, and most preferably about 2% or less of the determined antithrombin activity. The advantageous effect of the heparin derivative is enhanced, in a preferred embodiment, by using the heparin derivative in combination with an increased salt concentration. (See Examples 5, 6, 7 and 8).

Once the added thrombin has been complexed, the amount of uncomplexed, residual thrombin remaining in the assay mixture can be determined. Uncomplexed thrombin can be determined by any method known in the art, including, for example, clot-forming assays and chromogenic assays. In a clot-forming assay, the residual, uncomplexed thrombin is determined by adding fibrinogen and measuring the clotting time using a fibrometer. Alternatively, and preferably, a chromogenic assay is employed in which a chromogenic thrombin substrate is added to the incubated assay mixture and the amount of uncomplexed thrombin is measured with a spectrophotometer. Several suitable chromogenic substrates that develop color upon reaction with thrombin are known in the art, including SAR-PRO-ARG p-Nitroanilide, S-2238 (H-D-Phe-Pip-Arg-pNA), Spectrozyme-TH (H-D-CHT-Ala-Arg-pNA), CBS-34-47 (H-D)CHG-But-Arg-pNA) and 2AcOH-H-D-HHT-Ala-Arg-pNA, among others. SAR-PRO-ARG p-Nitroanilide (Sigma Chemical, St. Louis, Mo., Cat. No. T 1553) is a preferred thrombin substrate. After adding the chromogenic thrombin substrate to the incubated assay mixture, the mixture is further incubated, preferably at about 37° C., to allow the chromogenic thrombin substrate to react with the uncomplexed thrombin, and the color to develop. Either a rate measurement or an endpoint measurement is obtained using a spectrophotometer (405 nm with the preferred thrombin substrate). The rate measurement reports the change in absorbance per unit time, and is typically associated with automated analyzers. The endpoint measurement reports the absorbance of the mixture after a certain period of time (e.g. about 2 minutes). The thrombin reactions are stopped at an appropriate time by adding a stop reagent. Suitable stop reagents include glacial acetic acid (Sigma Chemical, St. Louis, Mo., Cat. No. A 6283), and 2% citric acid solution, formed, for example, from 2 g. citric acid monohydrate (Sigma Chemical, St. Louis, Mo., Cat. No. C 1909) in 100 ml water. Other stop reagents are known in the art.

The determined amount of uncomplexed thrombin is then correlated to the amount of antithrombin III which was originally present in the plasma sample being assayed. Generally, the ATIII content in the sample is inversely proportional to the determined uncomplexed thrombin. The determined uncomplexed thrombin is preferably correlated to ATIII using a standard curve. The standard curve should be prepared using the same laboratory equipment and methods as are employed for determining ATIII of a patient's plasma sample. Briefly, a standard curve is prepared by assaying plasma samples having known ATIII levels and then plotting the absorbance measurement (e.g. value or rate), typically on the y-axis, against the known ATIII concentration, typically on the x-axis. Once the standard curve is obtained, it can be used to determine unknown ATIII levels in a patient plasma sample by obtaining the absorbance measurement and then reading it against the curve to determine the corresponding ATIII level.

A preferred standard can be prepared as follows. A normal reference plasma (NRP), such as ACCUCLOT™ (Sigma Chemical, St. Louis, Mo., Cat. No. A7432), or a citrated normal plasma pool (NPP) with an assumed value of 100% normal is diluted using the preferred diluent composition described above. A 100%-ATIII standard plasma sample is prepared by combining the NRP or NPP (25 $\mu$l) with the diluent composition (975 $\mu$l). A 50%-ATIII standard plasma sample is prepared by further diluting the 100%-ATIII standard (500 $\mu$l) with the diluent composition (500 $\mu$l). A 0%-ATIII standard plasma sample can be the diluent composition (1000 $\mu$l) itself. In an equivalent protocol, the preferred standard samples can be prepared by serially diluting the NRP in physiological saline and then combining 25 $\mu$l of each diluted sample to 975 $\mu$l of the diluent composition.

An alternatively preferred standard curve can be prepared from a high-calibrator reference plasma to cover a wider range of ATIII concentrations. (See Example 9 and Example 10). While the high-calibrator reference plasma is described herein in connection with ATIII assays, its use is not limited to ATIII calibration. The high-calibrator reference plasma can be used as a standard for any plasma constituent, including for example, besides ATIII, other plasma proteins such as protein C, protein S, factor II, factor V, factor VIII, factor IX, factor X, factor XI, factor XII, kallikrein, prekallikrein, tPA, PAI-1, fibrinogen and plasminogen. Use of a high-calibrator reference plasma allows for determination of a plasma constituent (e.g. ATIII) in a patient plasma sample having higher than normal amounts of the constituent (e.g. over 110% normal), without having to reassay the sample in prediluted form in a second assay. Hence, the high-calibrator reference plasma can be used to construct standard curves that will encompass a wider range of high-end constituent values and will, thereby, avoid time consuming reassaying of high-end samples.

A high-calibrator reference plasma can be made by obtaining a normal reference plasma, lyophilizing a volume, $V_1$, of the normal reference plasma, and reconstituting the lyophilized normal reference plasma with deionized water to form a reconstituted plasma of a volume, $V_2$, where $V_2$ is less than $V_1$. $V_2$ is preferably an amount sufficient to form a reconstituted plasma having the plasma constituent at a concentration of about 120% of normal or greater, preferably at a concentration ranging from about 120% to about 175% of normal and most preferably ranging from about 130% to about 150% of normal. The ratio of the second volume to the first volume, $V_2:V_1$, preferably ranges from about 7:8 to about 1:8, more preferably from about 3:4 to about 1:4, even more preferably from about 3:4 to about 1:2, and is most preferably about 2:3. The resulting reconstituted plasma is the high-calibrator reference plasma which comprises a plasma constituent at a concentration of about 120% of normal or greater. The reference plasma preferably comprises a plasma constituent (indeed, each of the plasma constituents) at a concentration ranging from about 120% to about 175% of normal and most preferably ranging from about 130% to about 150% of normal.

The normal reference plasma employed in preparing a high-calibrator plasma reference is preferably human plasma. The normal reference plasma can be obtained from commercial sources or by pooling plasma samples from healthy individuals. Such normal plasma pools are typically citrated and have assumed value of 100% normal. Preferably at least about 7 units of human plasma are pooled. The pool may, if desired, be tested for ATIII content or for the content of any other plasma constituent for which the reference plasma will be used as a calibration standard. In general, the pool will be considered to have a value of 90% normal to 110% normal for ATIII. For other plasma constituents, the range of normal values may extend from 80% (e.g. Factor VIII) to 130% (e.g. Factor XII). Specific normal ranges for particular constituents besides ATIII are known in the art and/or can be readily determined by a skilled artisan by forming a normal pool as described herein and determining the particuluar constituent. The pooled plasma can be mixed with an appropriate buffer to obtain a pH ranging from about 6 to about 8.5, and preferably a pH of about 7.3. Glycine can also be added to the pooled plasma. The plasma can be mixed and then filtered to remove any particulates.

Regardless of how obtained, the normal reference plasma is dispensed into vials or other suitable containers at a volume, $V_1$, and then lyophilized according to methods known in the art. Generally, the plasma is frozen under vacuum at a temperature sufficient and for a period of time sufficient to form the lyophilized plasma. The temperature, vacuum and period of time are not narrowly critical, but lyophilization can be generally performed as follows. The plasma is frozen to a deep freeze temperature typically ranging from about −60° C. to about −20° C. without vacuum for a period of time ranging from about 2 hours to about 24 hours. A vacuum is then applied, preferably ranging from about 10 millitorr to about 200 millitorr. The shelf temperature is then raised somewhat, typically to a temperature ranging from about 0° C. to about 25° C., for a period of time sufficient to lyophilize the plasma. The lyophilization is, more preferably, performed by first deep-freezing the sample in a chamber to a temperature of about −40° C. without vacuum for a period of about 4 hours, then drawing a vacuum in the chamber of less than about 200 millitorr, and subsequently raising the temperature preferably to about 25° C. for a period sufficient for the product to reach about 25° C. for about 4 hours. In a preferred embodiment, 1.5 ml of a normal reference plasma is supplied to a vial and lyophilized by freezing for about 4 hours at −40° C. without vacuum. A vacuum of less than about 200 millitorr is subsequently applied, and the shelf temperature is raised to about 25° C. for a period of time sufficient to lyophilize the plasma sample. The lyophilized plasma sample is preferably sealed under vacuum. The lyophilized plasma sample can be stored, prior to reconstituting, for about 2 years at temperatures from about 2° C. to about 8° C.

For use, the lyophilized plasma sample is reconstituted with a suitable solvent to form a reconstituted plasma having a volume, $V_2$, as described above. Water is a preferred reconstituting solvent, and is deionized water is most preferred. However, other solvents and/or solutions, such as the aforedescribed heparin-derivative diluent composition or heparin-derivative-thrombin reagent composition can also be employed to reconstitute the lyophilized plasma sample. The high-calibrator reference plasma is, for the preferred embodiment discussed above, reconstituted with deionized water to 1.0 ml, such that the ratio of $V_2:V_1$ is 3:2. This effectively increases the concentration of all plasma constituents, including ATIII, to approximately 1.4 times their original concentration—effecting plasma constituent values of about 130%–140% normal. The high-calibrator plasma reference can be stored, in reconstituted form, for about 96 hours at about 2° C. to about 8° C. for ATIII. Storage times may vary for other plasma constituents.

It is preferable that the reconstituted plasma be calibrated against a verified primary or secondary, traceable standard before use in forming standard samples. For example, for use in connection with an ATIII assay, the high-calibrator reference plasma can be verified using the WHO $2^{nd}$ International Standard for Antithrombin, Plasma 93/768 (established 1994). (International Institute for Biological Standards and Controls, Potters Bar, U.K.). Verification can be done by diluting the reconstituted high-calibrator reference plasma with saline (e.g. 1:1), determining the value of the plasma constituent of interest (e.g. ATIII) against the verification standard, and then multiplying the determined value by the dilution factor (e.g., by 2 for a 1:1 dilution). A high-calibrator reference plasma prepared and verified as describe above should recover within typical assay specifications (typically 5–8%).

The verified high-calibrator reference plasma can be used to form standard calibration curves for any plasma constituent, as generally known in the art, and as described herein for ATIII. The verified high-calibrator reference plasma can be supplied, in kit form, as a reconstituted plasma solution, as a lyophilized high calibrator reference plasma. Alternatively, a kit can include (1) a lyophilized normal reference plasma comprising a plasma constituent at a concentration ranging from about 90% of normal to about 110% of normal, and (2) instructions to reconstitute the lyophilized reference plasma with a volume sufficient to form a reconstituted plasma which includes the plasma constituent at a concentration of about 120% of normal or greater, and preferably at the preferred ranges and concentrations of the high-calibrator reference plasma set forth above.

The ATIII assay, as set forth above, can be performed using manual or automated protocols, regardless of the reference plasma employed. In a preferred manual protocol, a plasma sample is obtained from a patient as described above. The plasma sample (25 µl) is diluted with the preferred heparin-derivative diluent composition (1000 µl) described above, which includes the preferred heparin derivative. The diluted plasma sample (200 µl) is incubated in a glass or plastic test tube at 37° C. for 2–4 minutes. The plasma sample is then combined with the preferred heparin-derivative-thrombin reagent composition (200 µl), described above, which includes the preferred heparin derivative and thrombin, to form an assay mixture. The assay mixture is then incubated at 37° C. for 2 minutes and then stopped using a stop reagent. The preferred chromogenic thrombin substrate (200 µl), described above, is then added to the incubated assay mixture, mixed, and incubated for 2 minutes to form a developed assay mixture. The reaction is then stopped. Water (200 µl) may, at this point, be optionally added to the developed assay mixture. The absorption is then read at 405 nm against a reagent blank prepared in the following order: 200 µl stop reagent, 200 µl diluent composition, 200 µl reagent composition, 200 µl chromogenic thrombin substrate, and if water is added to the developed assay mixture, 200 µl water. The absorbance obtained is then correlated against a standard curve prepared using the same protocols for samples having known amounts of ATIII, as described above.

In a preferred automated method, an AMELUNG AMAX CS-190™ Coagulation Analyzer can be used according to operational instructions. According to one approach, the analyzer is programmed to take 5 µl of undiluted plasma sample, to add 275 µl of the described heparin-derivativethrombin reagent composition to form an assay mixture, to incubate the assay mixture for 3 minutes at 37° C. and to then add 50 μl chromogenic thrombin substrate. The analyzer measures reaction kinetics (mE/min) after 20 seconds, 40 seconds and 60 seconds, and automatically calculates ATIII activity, reported as percent normal, from a calibration curve developed by reference calibration performed by the instrument. In an alternative automated approach, a diluted plasma sample can be employed, with appropriate programming of the analyzer to account for the dilution.

Kits for performing the described ATIII assay can include a heparin-derivative diluent composition, as described, a heparin-derivative-thrombin reagent composition, as described, and a chromogenic substrate. The kit can also include instructions for forming the assay mixture according to the methods provided herein. A diluent composition for a preferred kit includes a heparin derivative, preferably chondroitinase ACI-treated heparin, and a salt, preferably an alkali metal halide salt. A reagent composition for a preferred kit includes a heparin derivative, preferably chondroitinase ACI-treated heparin, a salt, preferably an alkali metal halide salt, and thrombin. The concentration of salt in the assay mixture prepared from these compositions according to the instructions of the kit preferably ranges from about 0.175 M to about 0.3 M.

In a preferred embodiment, the heparin-derivative diluent and the heparin-derivative-reagent composition are provided in the kit as lyophilized compositions. A lyophilized diluent composition comprises a heparin derivative. A lyophilized reagent composition comprises thrombin and a heparin derivative. The lyophilized compositions can also include an appropriate buffer, an inorganic salt, and additionally, surfactants, chelating agents, preservatives and other compounds commonly employed. A preferred lyophilized reagent composition preferably comprises chondroitinase ACI-treated heparin, thrombin, NaCl, TAPS, EDTA, Tween 80, gelatin, sodium azide, dextran and bovine serum albumin. A preferred lyophilized diluent composition is the same as the preferred reagent composition but without thrombin.

The lyophilized reagent composition can be prepared by lyophilizing a heparin-derivative-thrombin reagent solution in which the concentration of heparin derivative preferably ranges from about 0.5 U/ml to about 6 U/ml, more preferably from about 1.0 U/ml to about 2.5 U/ml, and is most preferably about 1.5 U/ml, and in which the concentration of thrombin preferably ranges from about 8 IU/ml to about 96 IU/ml, more preferably from about 16 IU/ml to about 40 IU/ml, and is most preferably about 24 IU/ml. These concentrations of heparin derivative and thrombin in the reagent solution (ie, as prepared for lyophilization) represent preferred ranges of from 1x to 12x of the preferred concentrations in the heparin-derivative-thrombin reagent composition (from which the aforedescribed assay mixture is preferably formed). The more preferred ranges are from 2x to 5x, with the most preferred concentration being a 3x composition.

The compositions can be lyophilized by freezing at a temperature and under vacuum for a period of time sufficient to form the lyophilized plasma. The temperature, vacuum and period of time are not narrowly critical, but lyophilization can be generally performed as follows. The compositions are frozen to a deep freeze temperature typically ranging from about −60 ° C. to about −20° C. without vacuum for a period of time ranging from about 2 hours to about 24 hours. A vacuum is then applied, preferably ranging from about 10 millitorr to about 200 millitorr. The shelf temperature is then raised somewhat, typically to a temperature ranging from about 0° C. to about 25° C., for a period of time sufficient to lyophilize the composition. The lyophilization is, more preferably, performed by first deep-freezing the composition in a chamber to a temperature of about −40° C. without vacuum for a period of about 4 hours, then drawing a vacuum in the chamber of less than about 200 millitorr, and subsequently raising the temperature preferably to about 25° C. for a period sufficient for the product to reach about 25° C. for about 4 hours. In a preferred embodiment, 4 ml of a the reagent solution is supplied to a vial and lyophilized by freezing for about 4 hours at −40° C. without vacuum. A vacuum of less than about 200 millitorr is subsequently applied, and the shelf temperature is raised to about 25° C. for a period of time sufficient to lyophilize the solution. The lyophilized composition is preferably sealed under vacuum. The lyophilized composition can be stored, prior to reconstituting, for about 2 years at temperatures from about 2° C. to about 8° C.

Significantly, the lyophilized reagent composition comprises both heparin derivative and thrombin in a single lyophilized composition. Unlike prior art approaches in which only one of the heparin or thrombin were lyophilized or in which heparin and thrombin were lyophilized as separate compositions, the lyophilized reagent composition allows for a simplified thrombin-based ATIII assay protocol. A reagent composition suitable for use in the ATIII assay can be obtained by reconstituting the lyophilized reagent composition with only water. While other reconstituting solvents or solutions could be employed as well, water, and preferably deionized water offers the most user-friendly assay protocol.

While the lyophilized reagent composition described above for use in connection with the present invention includes a heparin-derivative and thrombin, a lyophilized reagent composition comprising both unmodified heparin and thrombin could also be prepared to obtain the same advantages for use of unmodified heparin and thrombin in connection with other assay protocols. The concentration of unmodified heparin in a heparin-thrombin reagent composition solution prepared for use in forming a lyophilized heparin-thrombin-reagent composition can be the same described above for the heparin derivative.

The following examples illustrate the principles and advantages of the invention.

EXAMPLES

Example 1

Preparation of Heparin Derivative

A 50 mM sodium phosphate buffer was prepared with sodium phosphate monobasic and the pH was adjusted to 7.2. Sodium salt of heparin (grade A-1, Porcine Intestinal Mucosa, activity 170 USP units/mg Sigma Cat No. H3393) was used to make a 10,000 U/ml solution of heparin in the sodium phosphate buffer prepared above.

Chondoitinase AC (Sigma Catalog C2780, from *Flavobacterium heparinum* 0.5–1.5 U/mg, 1 unit causes a delta OD232 of 1.0/min due to release of unsaturated disaccharide from chondroitin sulfate A at pH 7.3 at 37C) was reconstituted in deionized water to 10U/ml immediately before use. The Chondroitinase AC was added to the heparin stock solution to give a final concentration of 1 unit/ml. Concentrations and or volumes were adjusted such that the ratio of chondroitinase AC to heparin was 1 unit/10,000 units.

The solution was mixed thoroughly, and the OD232 was determined using the phosphate buffer as a blanking solution. The mixture was then sealed and incubated at 37C for 24–48 hours. At the end of the incubation time the OD232 was again determined and an increase in OD of approximately 10% relative to the initial reading indicated that enzymatic digestion had occurred, and that disaccharides had been cleaved from the heparin to form heparin derivative. The vial was resealed and submerged in a boiling water bath for 5 minutes.

Example 2

Preparation of Heparin-Derivative-Thrombin Reagent Composition, Heparin-Derivative Diluent Composition, and Chromogenic Thrombin Substrate A heparin-derivative-thrombin reagent composition was prepared as follows. Thrombin (2–12 IU/ml) was added to a buffer containing, N-tris[hydroxymethyl]methyl-3-aminopropanesulfonic acid (TAPS—38 mM), 0.175M NaCl as well as ethylene diamine tetraacetic acid (EDTA—3.75 mM) tween 80 (polyoxyethylenesorbitan monooleate—0.015%), sodium azide (0.003%), gelatin (bovine, autoclaved—33 ug/ml), dextran (1.5%), bovine serum albumin (0.1%) polyethylene glycol (8000MW—0–1%) and chondroitinase AC-treated heterogeneous porcine heparin (0.5 U/ml) at pH 8.2.

A heparin-derivative diluent composition was prepared as described immediately above, but without thrombin.

A chromogenic thrombin substrate composition was prepared by dissolving sarcosyl-proline-arginine p-nitroanilide dihydrochloride to 2–3 mM in 1% mannitol.

Example 3

ATIII Assay with Chondroitinase ACI-Treated Heparin

ATIII assays were performed on two sets of standard plasma samples having known ATIII levels to create two standard curves—a reference curve and a HCII-normal curve.

A first set of standard plasma samples, referred to herein as reference samples, were used to prepare the reference curve. The reference samples were prepared from a 100%-ATIII normal reference plasma (NRP), Sigma Cat. No. A 7432, by diluting with saline to obtain 75%-ATIII, 50%-ATIII and 0%-ATIII reference samples having progressively lower levels of all plasma constituents—including both ATIII and HCII.

A second set of standard plasma samples, referred to herein as HCII-normal samples, were used to prepare the HCII-normal curve. These samples were prepared from a 100%-ATIII normal reference plasma (NRP) by diluting with an ATIII-immunodepleted plasma (Affinity Biologicals) having less than 1% normal ATIII level, but containing normal levels of heparin cofactor II (HCII). The HCII-normal samples had progressively lower levels of ATIII (75%-ATIII, 50%-ATIII and 0%-ATIII), with all other inhibitors, including HCII, remaining constant at its normal (100%-HCII) level.

ATIII assays were performed on each of the HCII-normal samples with protocols involving heparin derivative prepared according to Example I. The HCII-normal samples were diluted 1/40 in the heparin-derivative diluent composition, prepared according to Example II (25 µl plasma sample+975 µl diluent composition), and equilibrated to 37C. 200 µl of this mixture was mixed with 200 µl of the heparin-derivative-thrombin reagent composition prepared according to Example II and also equilibrated to 37C to form an assay mixture. The assay mixture, which included 175 mM sodium chloride, was incubated for 2 minutes at 37° C. 200 µl of the chromogenic thrombin substrate prepared according to Example II as was added to the incubated assay mixture and allowed to react with the uncomplexed thrombin for exactly 1 minute or exactly 2 minutes, depending on the relative concentrations of thrombin and substrate, to form a developed assay mixture. The reactions were stopped using 200 µl of glacial acetic acid or 2% citric acid. The absorbance of the developed assay mixture was read at OD405 using a spectrophotometer. A standard curve, designated as "HCII-normal/treated" was prepared by plotting the measured absorbance values (y-axis) against the known AT-III levels (x-axis) for the corresponding HCII-normal samples, as shown in FIG. 1 (triangles).

Control assays using unmodified porcine heparin were performed on each of the reference samples and, independently, on each of the HCII-normal samples. A heparin-diluent composition and a heparin-thrombin reagent composition were prepared as in Example II except that unmodified heparin was used in place of the chondroitinase AC-treated heparin. An ATIII assay employing these unmodified-heparin based compositions was then performed analogously to the assay described immediately above. The resulting standard curves are shown in FIG. 1 for the HCII-normal samples, designated as "HCII-normal/untreated" (open squares), and for the reference samples, designated as "reference/untreated" (closed squares).

Figure 1:
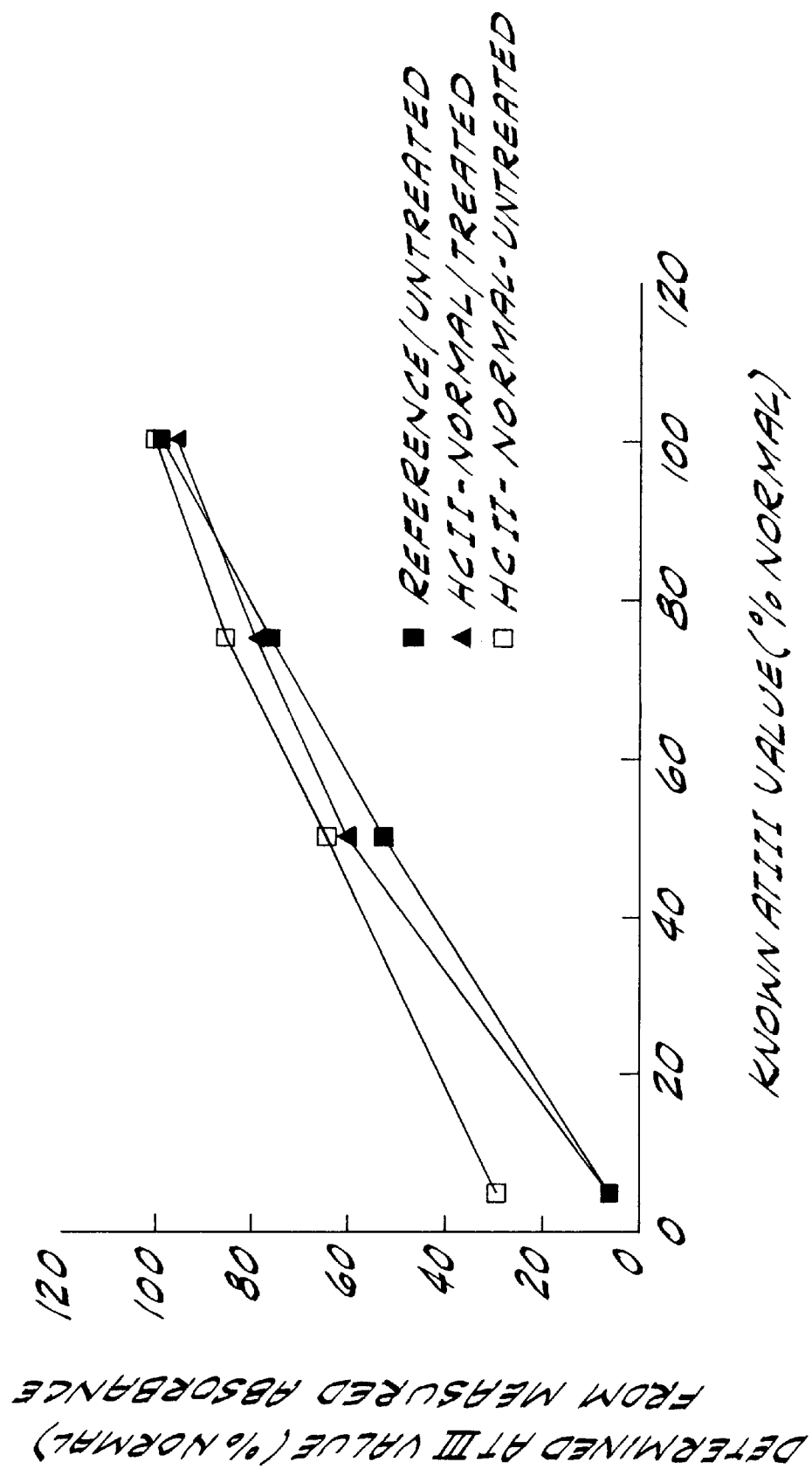
FIG. 1 shows determined ATIII values for plasma samples having various known ATIII concentrations. Reference samples were prepared by dilution of a normal reference plasma with saline, and HCII-normal samples prepared by dilution of a normal reference plasma with ATIII-deficient plasma (Affinity Biologicals) having less than 1% normal ATIII level, but containing normal levels of heparin cofactor II (HCII) as well as other plasma constituents. The reference samples were assayed using a thrombin-based assay with unmodified heparin (standard curve designated as "reference/untreated"—closed squares). The HCII-normal samples were assayed with a thrombin-based assay using unmodified heparin (standard curve designated "HCII-normal/untreated"—open squares), and independently, with the thrombin-based assay of the present invention using a heparin derivative prepared using chondroitinase AC (standard curve designated "HCII-normal/treated"—triangles). Values are reported in percent normals.

Referring to FIG. 1, the contribution of HCII to the determined antithrombin activity for thrombin-based assays employing unmodified heparin is shown by comparing the two control curves—the HCII-normal/untreated (open squares) and the reference/untreated curve (closed squares). The difference between the determined ATIII values for these curves at 5%-ATIII (where the reference/untreated plasma sample is known to contain 5%-ATIII and 5%-HCII and the HCII-normal/untreated plasma sample is known contain 5%-ATIII and 100%-HCII) represents the contribution to the determined activity made by non-ATIII inhibitors, predominantly HCII. Hence, the contribution of HCII to the determined ATIII activity for assays using unmodified heparin is about 25%.

In contrast, the contribution of HCII to the determined antithrombin activity for thrombin-based assays employing the preferred heparin derivative is shown by comparing the determined ATIII values for the HCII-normal/treated (triangles) and the HCII-normal/untreated standard curves of FIG. 1 at the known 5%-ATIII value. Although the assayed HCII-normal samples contained 100%-HCII, the HCII contributed only to the determined ATIII when unmodified heparin was used in the assay, and significantly, the HCII in these samples did not contribute to the determined ATIII levels when the heparin derivative was used in the assay.

Similar results were obtained using automated protocols in which an assay mixture having a ratio of diluted plasma sample:heparin-derivative-thrombin reagent:chromogenic thrombin substrate of 1:1:1 was used. In an alternative automated protocol, the plasma sample was mixed with the heparin-derivative-thrombin composition at a ratio of 1:55 in a total volume of 280 µl, and incubated for 30–180 seconds. Subsequently, 40–70 µl of the thrombin substrate was added, and the reaction rate was calculated by the instrument, and reported in terms of a % normal.

Example 4

ATIII Assay w/Unmodified Heparin and Various Concentrations of Sodium Chloride

In this example, ATIII assays were performed on reference samples and HCII-normal samples essentially as described in Example 3 using unmodified heparin in assay mixtures in which the sodium chloride concentration was varied from 175 mM to 600 mM. Standard curves were prepared for 175 mM and 310 mM samples. These curves are referred to herein and in FIG. 2 as "reference/untreated/ 0.175M" (closed squares), as "HCII-normal/untreated/ 0.175M" (diamonds), as "reference/untreated/0.310M" (triangles), and as "HCII-normal/untreated/0.310M (open squares).

Figure 2:
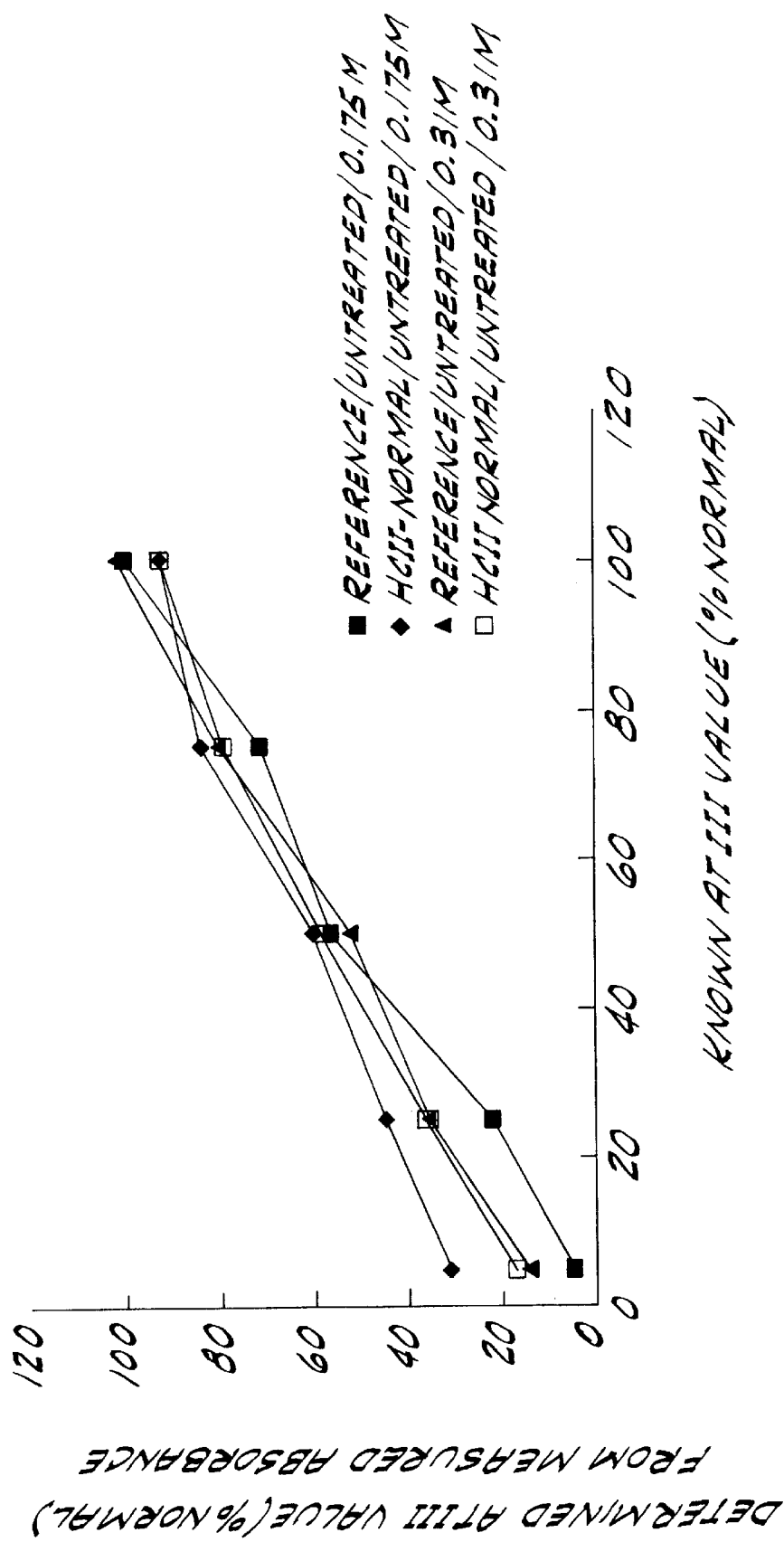
FIG. 2 shows determined ATIII values for plasma samples having various known ATIII concentrations. Reference samples were prepared by dilution of a normal reference plasma with saline, and HCII-normal samples were prepared by dilution of a normal reference plasma with ATIII-deficient plasma (Affinity Biologicals) having less than 1% normal ATIII level, but containing normal levels of heparin cofactor II (HCII) as well as other plasma constituents. The reference samples and the HCII-normal samples were assayed using unmodified heparin in assay mixtures in which the sodium chloride concentration was 175 mM or 310 mM, with the results designated as "reference/untreated/0.175M" (closed squares), as "HCII-normal/untreated/0.175M" (diamonds), as "reference/untreated/0.310M"

Referring to FIG. 2, the difference between the determined ATIII values at the known 5%-ATIII level for the reference/untreated/0.175M curve (closed squares) and the HCII-normal/untreated/0.175M curve (diamonds) represents the contribution of HCII to determined antithrombin activity using 175 mM sodium chloride—about 25%. The difference between the determined ATIII values at the known 5%-ATIII level for the reference/untreated/0.310M curve (triangles) and the HCII-normal/untreated/0.310M curve (open squares) represents the contribution of HCII to determined antithrombin activity using NaCl concentrations of 310 mM—about 5%. Hence an increase in salt concentration can improve a thrombin-based ATIII assay by decreasing the effect of HCII on determined antithrombin activity.

Example 5

ATIII Assay with Chondroitinase ACI-treated Heparin and with Increased Sodium Chloride Concentration ATIII assays were performed to observe the combined effect of using an assay mixture comprising a heparin derivative and higher salt concentrations. Reference samples and HCII-normal samples were assayed essentially as in Example 3 except using an assay mixture including chondroitinase AC-treated heparin and 310 mM sodium chloride, and, independently, using an assay mixture including unmodified heparin and 175 mM sodium chloride. The standard curves developed are referred to herein and in FIG. 3 as "reference/untreated/0.175M" (closed square), as "HCII-normal/untreated/0.175M" (diamonds), as "reference/treated/0.310M" (triangles), and as "HCII-normal/treated/0.310M" (open squares).

Referring to FIG. 3, the difference between the determined ATIII values at the known 5%-ATIII level for the reference/untreated/0.175M curve (closed squares) and the HCII-normal/untreated/0.175M curve (diamonds) represents the contribution of HCII to determined antithrombin activity using unmodified heparin in a 175 mM sodium chloride assay mixture—about 25%. In contrast, the difference between the determined ATIII values at the known 5%-ATIII level for the reference/treated/0.310M curve (triangles) and the for the HCII-normal/treated/0.310M curve represents the contribution of HCII to determined thrombin activity using the heparin derivative and a 310 mM NaCl assay mixture—about 6%.

Example 6

ATIII Assay of ATIII-Depleted Plasma

Standard plasma samples, referred to herein as ATIII-depleted samples, were prepared from an ATIII-immunodepleted plasma (Affinity Biologicals) having less than 1% normal ATIII level, but containing normal levels of heparin cofactor II (HCII) as well as other plasma constituents, by diluting with saline. The ATIII-depleted samples had progressively lower levels of HCII (75%-HCII, 50%-HCII, 25%-HCII and 0%-HCII), and each had less than 1%-ATIII.

The ATIII-depleted samples were assayed essentially as in Example 3 except using an assay mixture including chondroitinase AC-treated heparin and 310 mM sodium chloride, and, as an independent control, using an assay mixture including unmodified heparin and 175 mM sodium chloride. The standard curves developed are referred to herein and in FIG. 4 as "ATIII-depleted/untreated/0.175M" (closed square), and as "ATIII-depleted/treated/0.310M" (diamonds).

Referring to FIG. 4, the ATIII determined using the unmodified heparin at 175 mM salt (closed squares) varies with decreasing HCII concentrations, indicating that the HCII is contributing to the determined antithrombin activity in a dose-dependent manner. In contrast however, the ATIII determined using the heparin derivative and 310 mM salt is independent of HCII concentrations, and accurately determines the actual ATIII in each of the ATIII-dependent samples. The advantage of the ATIII assay of the present invention is also shown by comparing the ATIII-depleted/untreated/0.175M curve (closed square) with the ATIII-depleted/treated/0.310M (diamonds) at the HCII-100% position. This data shows that when ATIII is determined for plasma samples using known protocols (with unmodified heparin and 175 mM salt), that HCII contributes over 20% of the determined antithrombin activity. When ATIII is determined using the protocols of the present invention (with heparin derivative and 310 mM salt), however, the HCII contributes only about 2% of the determined thrombin activity.

Example 7

Correlation Studies Between ATIII Assay with Chondroitinase ACI-treated Heparin and Other ATIII Assays A study was conducted to compare the ATIII assay of the present invention (using a heparin derivative) to known thrombin-based ATIII assays (using unmodified heparin) and to known Factor Xa-based ATIII assays. A total of 116 plasma samples were involved in the study. The plasma samples were obtained from normal healthy donors and from patients with liver disease, disseminated intravascular coagulation (DIC), and type I and type II genetic ATIII deficiencies. A small number of samples were prepared from mixtures of ATIII depleted, HCII depleted and normal plasma.

Control samples were analyzed using FDA approved methods on automated instruments using a commercially available Factor Xa-based ATIII assay and a commercially available Factor IIa (thrombin)-based assay with unmodified heparin and sodium chloride levels of 175 mM. The ATIII assay of the present invention was used to measure the ATIII levels in the same samples according to the methods as set as set forth in Example 3, using an assay mixture having chondroitinase AC-treated heparin and NaCl concentration of 220 mM.

The assay results were subjected to regression analysis to determine the level of correlation between the methods. FIG. 5 and Table 1 compare the results for the ATIII assay of the present invention to those for the known thrombin-based assay (using unmodified heparin). FIG. 6 and Table 2 compare the results for the ATIII assay of the present invention to those for the Factor Xa-based assay. The correlation coefficient r indicates that the ATIII assay of the present invention correlates better with the Factor Xa-based assay (r=0.98) than with the known thrombin-based assay (r=0.93). Moreover, the correlation between the Factor Xa-based assay and the known thrombin-based assay (with unmodified heparin) was even lower (r=0.89, y=1.07x–6.26). This data indicates that the present ATIII assay correlates more closely to the HCII-independent Xa based assay, than to heretofore known Factor IIa-based ATIII assays involving unmodified heparin.

TABLE 1

ATIII Assay - Automated (Amelung-AMAX)
New Thrombin-Based ATIII Assay vs
Known Thrombin-Based ATIII Assay Regression Output:

| | |
|---|---|
| Constant | −2.8748223 |
| Standard Err of Y Estimated | 9.12998044 |
| R Squared | 0.85751825 |
| R | 0.92602281 |
| Number of Observations | 116 |
| Degrees of Freedom | 114 |
| X Coefficient(s) | 1.03629444 |
| Standard Err of Coefficient(s) | 0.03956295 |

Y = 1.03 x −2.88

TABLE 2

ATIII Assay - Automated (Amelung-AMAX)
Known Xa Assay vs New Thrombin-Based ATIII Assay Regression Output:

| | |
|---|---|
| Constant | 7.85729778 |
| Standard Err of Y Estimated | 5.06453959 |
| R Squared | 0.95615708 |
| R | 0.97783285 |
| Number of Observations | 116 |
| Degrees of Freedom | 114 |
| X Coefficient(s) | 0.91307889 |
| Standard Err of Coefficient(s) | 0.01831222 |

Y = 0.91 x +7.85

Example 8

Differentiation of Normal and Abnormal Patient Populations in Clinical Studies using Various ATIII Assays ATIII levels were established for a population of healthy volunteers using a Factor Xa-based assay, a known thrombin-based assay (using unmodified heparin with a salt concentration of 175 mM), and the thrombin-based assay of the present invention (using a heparin derivative prepared with chondroitinase AC with a NaCl concentration of 220 mM). Thirty patient samples were selected which were determined to be abnormal (ATIII<75% normal) based on the Factor Xa-based assay, and these samples were compared to the values obtained for the same samples using the known thrombin-based assay and the thrombin-based assay of the present invention.

Ranges were determined for the normal and abnormal populations based on raw data and also calculated from the mean plus or minus two standard deviations of the mean. The determined ranges based on raw data are presented in FIG. 7. These ranges show that both the Factor Xa-based assay and the thrombin-based assay of the present invention were able to distinguish between normal and abnormal samples. That is, the lowest values for normal samples were clearly separated from the highest values for abnormal samples when ATIII was determined using these protocols. However, the known thrombin-based assay is not able to distinguish between some normal and abnormal plasma samples, as shown by the overlap between the lowest values for normal samples and the highest values for abnormal samples. The same differentiations and overlaps are observed for the mean ±2SD data (data not shown).

Example 9

Preparation of High Calibrator Reference Plasma

A normal reference plasma was prepared from a pool of 7 units of normal human plasma. The pooled plasma was mixed with a hepes/propionic acid buffer concentrate (2 M Hepes/40 g/l propionic acid) and glycine (Sigma catalog G7126—10 g/l). The bufferred plasma was mixed and filtered to remove any particulates, and then dispensed into vials at a volume of 1.5 ml. Rubber stoppers were loosely applied. The vials were transferred to a lyophilizer (freeze dryer) and frozen without vacuum for 2–4 hours at −40° C. A vacuum was then applied (<200 millitorr), and the shelf temperature was set for 25C. When the plasma had reached 25° C. for 4 hours, the shelves were moved together to seal the caps on the vials under vacuum.

The lyophilized normal reference plasma was reconstituted with deionized water to 1.0 ml to form the high-calibrator plasma reference. This effectively increased the concentration of all plasma proteins, including ATIII, to approximately 1.4 times their original concentration.

The high-calibrator reference plasma was verified against a the WHO $2^{nd}$ International Standard for Antithrombin, Plasma 93/768 (established 1994). (International Institute for Biological Standards and Controls, Potters Bar, U.K.). Briefly, 16 to 24 vials of the high-calibrator reference material were diluted 1:1 with saline and then assayed for ATIII according to the methods of the present invention, in duplicate sets of experiments, using standard curves prepared from the verification standard. The determined ATIII value was multiplied by a dilution factor of 2, and indicated that the high-calibrator reference plasma had increased high-end range of 130%–140% normal.

Example 10

ATIII Assays Using the High-Calibrator Reference Plasma as a Standard

A standard curve was constructed as described in Example 3 using the high-calibrator reference plasma prepared as described in Example 9. The standard curve included a high-end ATIII values of up to about 140% of normal. The standard curve prepared from the high-calibrator reference plasma was employed to directly assay patient plasma samples having ATIII levels greater than about 120% of normal. Data from such direct high-end ATIII assays is included in the data presented in FIG. 5 and FIG. 6 (See Example 7) and in FIG. 7 (See Example 8).

Example 11

Preparation of Lyophilized Heparin-Derivative-Thrombin Reagent Composition

The heparin-derivative-thrombin reagent solution was prepared as set forth in Example 2, except with a concentration of heparin derivative of about 1.5 U/ml, and with a concentration of thrombin of about 24 IU/ml. The reagent solution was dispensed into vials at a volume of 4 ml. Rubber stoppers were loosely applied. The vials were transferred to a lyophilizer (freeze dryer) and frozen for 2–4 hours at −40 0C. A vacuum was then applied (<200 millitorr), and the shelf temperature was set for 25° C. When the composition had reached 25° C. for 4 hours the shelves were moved together to seal the caps on the vials under vacuum.

In separate runs, additional reagent solutions were prepared with the concentration of heparin varying from about 0.5 U/ml to about 6 U/ml and with the concentration of thrombin ranging from about 8 IU/ml to about 96 IU/ml. These solutions were lyophilized essentially as described above.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

I claim:

1. A method for determining antithrombin III in a plasma sample, the method comprising
   combining the plasma sample with thrombin and with a heparin derivative, the heparin derivative being prepared by reacting heparin with an enzyme, to form an assay mixture,
   forming a complex between the antithrombin III and the thrombin in the assay mixture,
   determining the uncomplexed thrombin in the assay mixture, and
   correlating the determined uncomplexed thrombin to the antithrombin III in the plasma sample.

2. The method of claim 1 wherein the heparin derivative is prepared by reacting heparin with an enzyme to form the heparin derivative and one or more disaccharides.

3. The method of claim 1 wherein the heparin derivative is prepared by reacting heparin with an enzyme to form a modified heparin composition comprising the heparin derivative and one or more disaccharides, and the assay mixture is formed by combining the plasma sample with the thrombin and with the modified heparin composition.

4. The method of claim 1 wherein the heparin derivative is prepared by reacting heparin with a chondroitinase.

5. The method of claim 1 wherein the heparin derivative is prepared by reacting heparin with a chondroitinase to form a modified heparin composition comprising the heparin derivative and one or more disaccharides, and the assay mixture is formed by combining the plasma sample with the thrombin and with the modified heparin composition.

6. The method of claim 1 wherein the heparin derivative is chondroitinase ACI-treated heparin.

7. The method of claim 1 wherein the assay mixture further comprises an alkali-metal halide salt at a concentration ranging from about 0.175 M to about 0.3 M.

8. The method of claim 1 wherein the assay mixture further comprises sodium chloride at a concentration of about 0.22 M.

9. The method of claim 1 wherein the heparin derivative is a chondroitinase-treated heparin and the assay mixture further comprises an alkali-metal halide salt at a concentration ranging from about 0.175 M to about 0.3 M.

10. The method of claim 1 wherein the heparin derivative is chondroitinase ACI-treated heparin and the assay mixture further comprises sodium chloride at a concentration of about 0.22 M.

11. The method of claim 1 wherein the heparin derivative is combined with the plasma sample to form a heparinized plasma sample and then the thrombin is combined with the heparinized plasma sample.

12. The method of claim 1 wherein the heparin derivative and the thrombin are combined with the plasma sample at the same time.

13. The method of claim 1 wherein the heparin derivative is combined with the plasma sample to form a heparinized plasma sample and then both the thrombin and additional heparin derivative are combined with the heparinized plasma sample at the same time.

14. A method for determining antithrombin III in a plasma sample, the method comprising
   preparing an assay mixture comprising the plasma sample, exogenous thrombin, and a heparin derivative effective for enhancing formation of a thrombin-antithrombin III complex, and being less effective than unmodified heparin for enhancing heparin cofactor II activity against thrombin,
   incubating the assay mixture,
   determining the uncomplexed thrombin in the incubated mixture, and
   correlating the determined uncomplexed thrombin to the antithrombin III in the plasma sample.

15. The method of claim 14 wherein the heparin derivative is at least 2 times less effective than the unmodified heparin for enhancing the heparin cofactor II activity against the thrombin.

16. The method of claim 14 wherein the heparin derivative is at least 4 times less effective than the unmodified heparin for enhancing the heparin cofactor II activity against the thrombin.

17. The method of claim 14 wherein the heparin derivative is at least 5 times less effective than the unmodified heparin for enhancing the heparin cofactor II activity against the thrombin.

18. A method for determining antithrombin III in a plasma sample containing endogenous heparin cofactor II, the method comprising
   preparing an assay mixture comprising the plasma sample, exogenous thrombin, and a heparin derivative,
   incubating the assay mixture,
   determining the uncomplexed thrombin in the incubated assay mixture, and
   correlating the determined uncomplexed thrombin to the antithrombin III in the plasma sample,
   wherein the endogenous heparin cofactor II contributes about 15% or less to the determined inhibition of thrombin by the antithrombin III.

19. The method of claim 18 wherein the endogenous heparin cofactor II contributes 10% or less to the determined inhibition of thrombin by the antithrombin III.

20. The method of claim 18 wherein the endogenous heparin cofactor II contributes 5% or less to the determined inhibition of thrombin by the antithrombin III.

21. A method for determining antithrombin III in a plasma sample, the method comprising
   obtaining a modified heparin composition comprising a heparin derivative and one or more disaccharides prepared by enzymatically digesting heparin, preparing an assay mixture comprising the plasma sample, exogenous thrombin, and the modified heparin composition, incubating the assay mixture, determining the uncomplexed thrombin in the incubated assay mixture, and correlating the determined uncomplexed thrombin to the antithrombin III in the plasma sample.

22. The method of claim 21 wherein the modified heparin composition is prepared by enzymatically digesting heparin with a chondroitinase.

23. The method of claim 21 wherein the modified heparin composition is prepared by enzymatically digesting heparin with chondroitinase ACI.

24. The method of claim 21 wherein the assay mixture further comprises an alkali-metal halide salt at a concentration ranging from about 0.175 M to about 0.3 M.

25. The method of claim 21 wherein the modified heparin composition is prepared by enzymatically digesting heparin with chondroitinase ACI, the assay mixture further comprises an alkali-metal halide salt at a concentration of about 0.22 M, and the uncomplexed thrombin is determined using a chromogenic thrombin substrate.

26. A reagent useful in a thrombin-based antithrombin III assay, the reagent comprising a lyophilized composition comprising (1) thrombin and (2) a heparin derivative prepared by reacting heparin with an enzyme.

27. The reagent of claim 26 wherein the lyophilized composition comprises the thrombin and a the heparin derivative.

28. The reagent of claim 26 wherein the lyophilized composition comprises the thrombin and a modified heparin composition comprising the heparin derivative and one or more disaccharides prepared by enzymatically digesting heparin.

29. The reagent of claim 26 wherein the lyophilized composition is prepared by lyophilizing a reagent solution comprising (1) the thrombin at a concentration ranging from about 8 IU/ml to about 96 IU/ml, and (2) the heparin derivative at a concentration ranging from about 0.5 U/ml to about 6 U/ml.

30. A kit for a thrombin-based antithrombin III assay useful to determine antithrombin III in a plasma sample, the kit comprising a diluent composition comprising a chondroitinase ACI-treated heparin and an alkali metal-halide salt, a reagent composition comprising a chondroitinase ACI-treated heparin, an alkali metal-halide salt and thrombin, a chromogenic thrombin substrate.

31. The kit of claim 30 further comprising instructions, wherein the reagent composition and, if present, the diluent composition, have a salt concentration such that the assay mixture formed by combining the plasma sample with the reagent composition and, optionally, with the diluent composition according to the instructions has a salt concentration ranging from about 0.175 M to about 0.3 M.

32. The kit of claim 30 wherein the alkali metal salt is sodium chloride and further comprising instructions, wherein the reagent composition and, if present the diluent composition, have a sodium chloride concentration such that the assay mixture formed by combining the plasma sample with the reagent composition and, optionally, with the diluent composition according to the instructions has a NaCl concentration of about 0.22 M.

* * * * *